(12) United States Patent
Watanabe et al.

(10) Patent No.: US 6,368,629 B1
(45) Date of Patent: Apr. 9, 2002

(54) COLON-SPECIFIC DRUG RELEASE SYSTEM

(75) Inventors: Shunsuke Watanabe; Hitoshi Kawai; Masataka Katsuma; Muneo Fukui, all of Shizuoka (JP)

(73) Assignee: Yamanouchi Pharmaceutical Company Ltd., Tokyo (JP)

( * ) Notice: Subject to any disclaimer, the term of this patent is extended or adjusted under 35 U.S.C. 154(b) by 0 days.

(21) Appl. No.: 09/183,339

(22) Filed: Oct. 30, 1998

Related U.S. Application Data

(63) Continuation of application No. 08/732,329, filed on Oct. 17, 1996, now abandoned, which is a continuation of application No. PCT/JP95/00766, filed on Apr. 19, 1995.

(30) Foreign Application Priority Data

Apr. 22, 1994 (JP) .............................................. 6-85114

(51) Int. Cl.$^7$ ........................... A61K 9/32; A61K 47/36
(52) U.S. Cl. ...................................... 424/482; 424/468
(58) Field of Search ................................ 424/484, 486, 424/482

(56) References Cited

U.S. PATENT DOCUMENTS

| | | | |
|---|---|---|---|
| 3,431,338 A | | 3/1969 | Munzel |
| 4,863,744 A | * | 9/1989 | Urquhart et al. ............ 424/484 |
| 4,968,508 A | * | 11/1990 | Oren et al. ................. 424/468 |
| 5,525,634 A | * | 6/1996 | Sintou et al. ............... 514/777 |
| 5,656,290 A | * | 8/1997 | Aelm et al. ................. 424/485 |
| 5,656,294 A | * | 8/1997 | Friend et al. ............... 424/485 |
| 5,840,322 A | * | 11/1998 | Friend et al. ............... 424/464 |
| 5,866,619 A | * | 2/1999 | Sintou et al. ............... 514/777 |

FOREIGN PATENT DOCUMENTS

| | | |
|---|---|---|
| EP | 0453001 | 10/1991 |
| EP | 0460921 | 12/1991 |

OTHER PUBLICATIONS

P.B. Deasy et al Proceed. Intl. Symp. Control. Release Biol. Mater. 24 279–280, Jun. 1997.*
WO 87/01588A.
WO 91/16881A.
WPI Abstract corresponding to JP 04 264021A.

* cited by examiner

Primary Examiner—Peter F. Kulkosky
(74) Attorney, Agent, or Firm—Townsend and Townsend and Crew LLP

(57) ABSTRACT

A system for releasing a drug specifically in the colon of the gastrointestinal tract, which comprises a drug (b) coated with an organic acid-soluble polymer material (a), and a saccharide (c) which rapidly generates an organic acid by the action of enterobacteria in the lower part of the gastrointestinal tract; a colon-specific drug release oral preparation, which comprises a composition comprising a drug (b) coated with an organic acid-soluble polymer material (a) and a saccharide (c) which rapidly generates an organic acid by the action of enterobacteria in the lower part of the gastrointestinal tract, said composition being coated with an enteric coating polymer material (d).

The invention provides a drug release system and a preparation which utilize enterobacteria, which do not form harmful substances due to the release-starting mechanism, show rapid degradation, and have higher colon specificity.

16 Claims, 9 Drawing Sheets

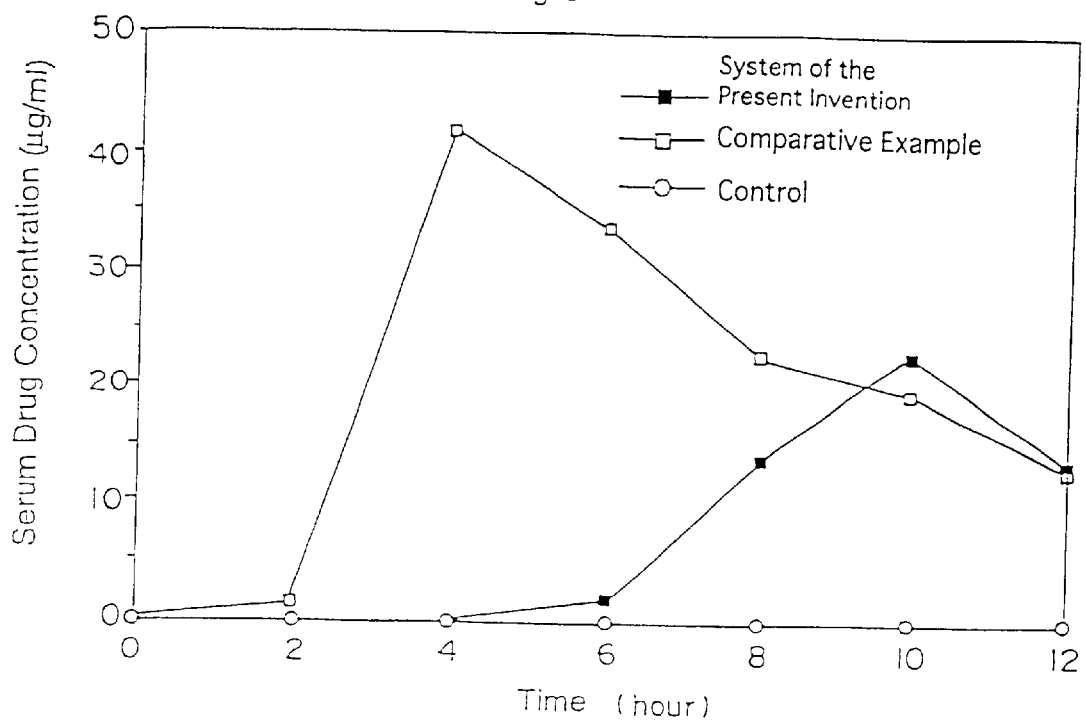
Fig. 3
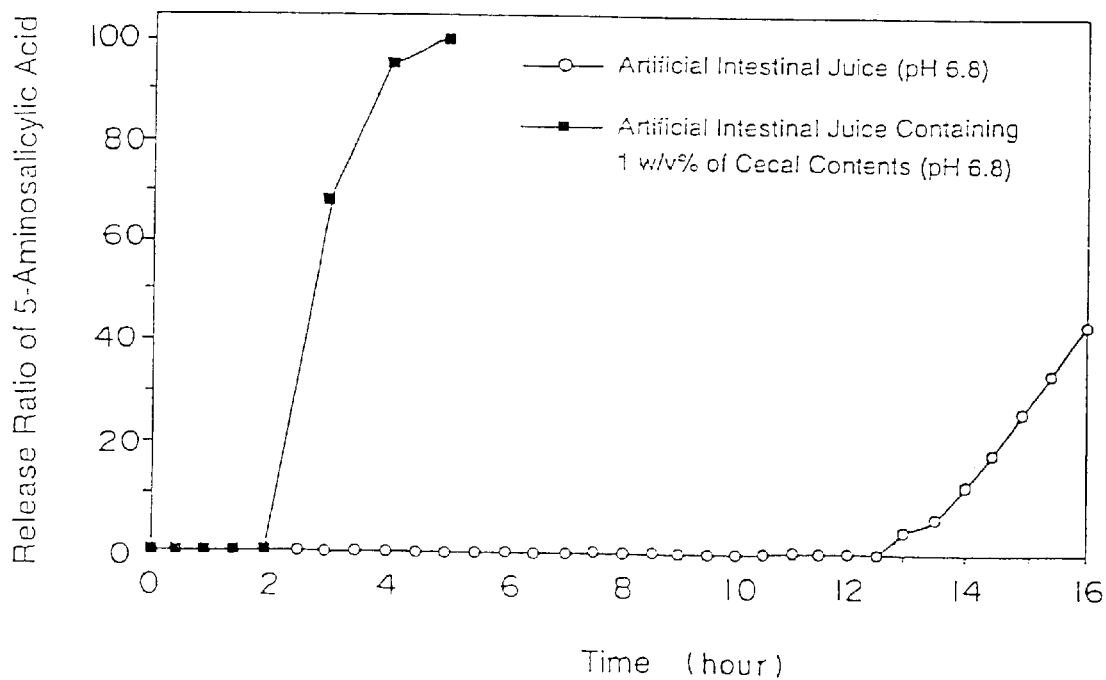
Fig: 4

COLON-SPECIFIC DRUG RELEASE SYSTEM

This application is a continuation of Ser. No. 08/732,329 filed Oct. 17, 1996 and now abandoned, which is a continuation of PCT/JP95/00766, filed Apr. 19, 1995.

TECHNICAL FIELD

The present invention relates to a drug release system and particularly a system for releasing a drug specifically in the colon of the gastrointestinal tract. More particularly, the present invention relates to a system for releasing a drug specifically in the colon of the gastrointestinal tract, which comprises a drug (b) coated with an organic acid-soluble polymer material (a) and a saccharide (c) which rapidly generates an organic acid by the action of enterobacteria in the lower part of the gastrointestinal tract; and a colon-specific drug release oral composition which comprises a composition comprising a drug (b) coated with an organic acid-soluble polymer material (a), and a saccharide (c) which rapidly generates an organic acid by the action of enterobacteria in the lower part of the gastrointestinal tract, the composition being coated with an enteric coating polymer material (d).

BACKGROUND OF THE INVENTION

In past ten years, rapid development occurred in the field of drug delivery or release. In particular, a number of drug delivery or release systems have been developed, having an influences on drug release control.

In the topical treatment of ulcerative colitis, etc., drug release in the colon of the gastrointestinal tract topically accumulates the drug in a high concentration without involving absorption in the small intestine, which leads to reduction of systemic side effects and is obviously favorable for improvement of therapeutic effect. Considering a systemic drug, on the other hand, release in the colon is disadvantageous in that the colon is shorter And poorer in development of microvilli than the small intestine and therefore has a smaller surface area available for absorption and is less permeable to a polar compound. However, the average retention time in the ascending colon is about 3 hours in younger people and about 10 hours in older people (see Hongo, et al., *NICHIHEIKATSUKINSHI*, 24, 55–60, 1988), which is equal to or even longer than that in the small intestine (about 3 to 4 hours), and it means long effective absorption time. Considering the aspect of the colon as a site of administration of peptide or protein-based drugs, the colon is advantageous in that no digestive enzymes is secreted and that the peptidase activity of the membrane of the large intestine is lower than that of the small intestine (Kopecek, et al., *Proc. int. Symp. Control. Rel. Bioact. Mat.*, 17, 130–131 (1990)). Therefore, a drug release in the colon is expected to give improved systemic bioavailability.

A large number of preparations targeting the lower part of gastrointestinal tract, especially the colon, have been reported. These systems are roughly divided into four types: the first is a delayed release system designed to release a drug in agreement with change in pH, the second is a timed-release system designed to release a drug after a predetermined time, the third is a microflora enzyme system making use of the abundant enterobacteria in the lower part of the gastrointestinal tract, and the fourth is a system making use of a lectin-like substance specific to the large intestine.

The first delayed release system is a system that uses an acrylic or cellulosic enteric coating material and dissolves on pH change. Because of ease of preparation, many reports on this system have been made. Taking the system using an acrylic enteric coating material, Eudragit S as an example, many reports can be found, such as those by Behringer, Manchester University, Saale Co., and the like. However, the group of Manchester University made a report at AAPS in 1993 on their single unit preparations using an enteric coating material, revealing that the timing of drug release is decided by the transit of the preparation in the gastrointestinal tract rather than pH change and, therefore, the specificity to the colon is low. It is very likely that the other similar delayed release systems are also unsuccessful in colon-specific drug release.

The second timed release system is represented by Time Erosion System (TES) by Fujisawa Pharmaceutical Co., Ltd. and Pulsincap by R. P. Scherer. According to these systems, the site of drug release is decided by the time of transit of a preparation in the gastrointestinal tract, which makes it difficult to release a drug certainly in the targeted lower part of the gastrointestinal tract. Since the transit of a preparation in the gastrointestinal tract is largely influenced by the gastric emptying time, some preparations are made enteric. Nevertheless, it is difficult to release a drug specifically in the colon, considering that the transit time of a preparation in the small intestine has the intra- and inter-variation and also largely varies according to the disease as reported.

The third system making use of the enterobacteria has recently increased in number. The system is classified into those utilizing degradation of azoaromatic polymers by an azo reductase produced from enterobacteria as reported by the group of Ohio University (M. Saffran et al., *Science*, Vol. 233: 1081 (1986)) and the group of Utah University (J. Kopecek et al., *Pharmaceutical Research*, 9(12), 1540–1545 (1992)); and those utilizing degradation of polysaccharides by β-galactosidase of enterobacteria as reported by the group of Hebrew University (unexamined published Japanese patent application No. 5-508631 based on a PCT application) and the group of Freiberg University (K. H. Bauer et al., *Pharmaceutical Research*, 10(10), S218 (1993)). In addition, the system using chitosan degradable by chitosanase by Teikoku Seiyaku K.K. (unexamined published Japanese patent application No. 4-217924 and unexamined published Japanese patent application No. 4-225922) is also included. Of these systems, degradation of an azoaromatic polymer by enterobacteria is slow (J. Kopecek et al., *Pharmaceutical Research*, 9(12), 1540–1545 (1992)) and has a fear of producing a harmful substance originated in an azo linkage so that the system may be unsuitable for long-term use. An insulin-containing preparation according to this system was actually administered to beagle dogs only to manifest low effects (M. Saffran et al., *Biochemical Society Transactions*, 18(5), 752–754 (1990)). The system using a polysaccharide is considered to cause no safety problem because a material that has been taken as dietary fiber is used. However, according to the report of the group of Nottingham University, pectin is slowly degraded by enterobacteria, and a drug is released earlier in an artificial intestinal juice (W. G. Cook et al., *Pharmaceutical Research*, 10(10), S223 (1993)). Therefore, this system cannot be regarded to be a colon-specific drug release system. Similarly, the drug release in an artificial intestinal juice is uncontrollable in the report by Hebrew University.

The fourth system utilizing a lectin-like substance present in the large intestine has been reported by Kopecek et al. of Utah University (J. Kopecek et al., *Proc. Int. Symp. Control. Rel. Bioact. Mat.*, 17, 130–131 (1990)). This technique relates to a polymer preparation prepared by binding fucose and a drug to a polymer via an azo bond, which is to utilize a lectine-like substance present in the guinea pig's large intestine, recognizing fucose and to control transit of the preparation in the colon so as to let the preparation release the drug by the action of an azo reductase. However, the fucose-recognizing lectin is specific to guinea pigs, and not found in rats. Therefore, the technique cannot be applied directly to humans.

As described above, any of the various systems heretofore proposed for drug release in the colon is unsatisfactory.

The inventors of the present invention made studies with paying their attention to the third system using enterobacteria.

Bacteria which live within the body are abundant in the oral cavity, rare in the stomach due to the acidicity, and also scarce in the upper part of the small intestine. The enterobacteria increases drastically in the order of the ileum, the cecum, and the colon. It has been reported that saccharides remaining undigested are degraded by enterobacterial in the part from the cecum to the ascending colon to make that part weakly acidic (pH of about 5) (S. S. Davis, *Novel Drug Delivery* and its *Therapeutic Application*, p. 89–101, edited by L. F. Prescott, W. S. Nimmo printed by John Willey & Sons. New York).

According to the Evans' report (Gut, 29, p. 1035–1041 1988), the average pH in the middle part of the small intestine is 6.6 and that in the cecum is 6.4, i.e., there is little change in pH between these two sites. In another report, Evans says that the pH of the cecum is from 4.5 to 7.5, which means large variations among individuals. Other researchers have reported that the pH is not decreased in the cecum. It is considered that the pH in the cecum is controllable to some extent by a diet in experimental animals but uncontrollable in humans.

A need has therefore been demanded to develop a site-specific drug release system which is not influenced by pH variation in the vicinities of the cecum with individuals and by diets and is designed to release a drug specifically in the colon without relying on time control.

DISCLOSURE OF THE INVENTION

In their study on colon-specific drug release systems, the inventors of the present invention have considered that generation of an organic acid by taking advantage of enterobacteria, if possible, would make it possible to release a drug protected by a coat that is dissolved by an organic acid, thereby providing a colon-specific drug release system which is unaffected by the pH in the vicinity of the cecum and does not rely on time control. Carbohydrates, particularly saccharides, are first to be considered as a material degradable by enterobacteria to generate an organic acid. Saccharides that have conventionally been used as components of preparations are degraded by the digestive enzymes in the gastrointestinal tract or directly absorbed from the gastrointestinal tract. Hence, the inventors paid their notice to the fact that, among the saccharides which have scarcely been used as a component of pharmaceutical preparations, there are saccharides neither digested by digestive enzymes nor absorbed from the gastrointestinal tract. Such saccharides include lactulose, raffinose, cellobiose, stachyose, and fructooligosaccharides.

The inventors have first examined whether lactulose is degraded or not by enterobacteria present in the lower part of the gastrointestinal tract. As a result, it was found unexpectedly that lactulose is degraded rapidly to generate an organic acid. The inventors have then found that, when a drug (b) coated with an organic acid-soluble polymer material (a) is delivered to the lower part of the gastrointestinal tract together with lactulose, lactulose is degraded by enterobacteria to rapidly generate an organic acid, whereupon the polymer material (a) is dissolved to release the drug (b) specifically in the colon. The present invention has been completed based on this finding.

As a result of further investigation, the inventors have found that even a material that is degraded by digestive enzymes or absorbed directly through the gastrointestinal tract can also be used similarly to lactulose as far as it is degradable by enterobacteria to easily generate an organic acid, since it is possible to coat such a material with an enteric coating polymer material (d) (i.e., a polymer material which is not dissolved in the stomach but in the small intestine) so that the material can easily be delivered to the lower part of the gastrointestinal tract. In this case, in order to deliver the material to the lower part of the gastrointestinal tract more efficiently, it is preferable that the material be coated first with the organic acid-soluble polymer material (a) and then with the enteric coating polymer material (d).

From the structural viewpoint, the material which generates an organic acid by the action of enterobacteria is considered to include carbohydrates particularly saccharides and derivatives thereof such as sugar alcohols. Taking into account the conditions of the lower gastrointestinal tract where enterobacteria live, water solubility would be of importance for the material to generate an organic acid rapidly. As a result of various studies, it was found that lactose having medium water solubility and ribose having low water solubility hardly dissolve with such a small amount of water that has passed through the coating layer of the organic acid-soluble polymer material (a) and therefore show no rapid generation of an organic acid. On the other hand, sucrose, glucose, xylose, fructose, maltose, and galactose having high water solubility were proved to generate an organic acid rapidly, which is similar to lactulose. With reference to sugar alcohols, on the other hand, rapid generation of an organic acid was not observed even with sorbitol and xylitol having high solubility as well as mannitol having medium water solubility and maltol having low solubility. Accordingly, it has now ascertained that saccharides having high water solubility are especially suitable as a material for rapidly generating an organic acid.

That is, the present invention relates to a system for releasing a drug specifically in the colon of the gastrointestinal tract. More particularly, it relates to a colon-specific drug release system, which comprises a drug (b).coated with an organic acid-soluble polymer material (a) and a saccharide (c) which rapidly generates an organic acid by the action of enterobacteria in the lower part of the gastrointestinal tract.

The system of the present invention is preferably embodied by coating the polymer material (a)-coated drug (b) and the organic acid-generating saccharide (c) with an enteric coating polymer material (d) in order to deliver them to the lower gastrointestinal tract. More specifically, there are two embodiments that the drug (b) and the saccharide (c) can be formulated separately or in the same composition as follows.

1) Formulation in separate compositions:

A system for releasing a drug specifically in the colon of the gastrointestinal tract, which comprises a composition (1) in which an organic acid-soluble polymer material (a)-coated drug (b) is further coated with an enteric coating polymer material (d), and a composition (2) comprising a saccharide (c) which rapidly generates an organic acid by the action of enterobacteria in the lower part of the gastrointestinal tract, which saccharide may optionally be coated with an enteric coating polymer material (d). The compositions (1) and (2) can be administered as a single preparation or separately prepared preparations.

2) Formulation in one composition:

A system for releasing a drug specifically in the colon of the gastrointestinal tract, which comprises a composition containing an organic acid-soluble polymer material (a)-coated drug (b) and a saccharide (c) which rapidly generates an organic acid by the action of enterobacteria in the lower part of the gastrointestinal tract, the composition being coated with an enteric coating polymer material (d).

In this composition, the saccharide (c) can be used either as a mixture with the drug (b) or as a coating layer on the drug (b). The latter system includes an embodiment in which the polymer material (a)-coated drug (b) is coated with the saccharide (c), an embodiment in which the saccharide (c)-coated drug (b) is coated with the polymer material (a), and an embodiment in which the drug (b) is coated with the saccharide (c) and the polymer material (a).

The present invention also relates to a colon-specific drug release oral composition, more particularly to a colon-specific drug release oral composition, which comprises a composition comprising a drug (b) coated with an organic acid-soluble polymer material (a), and a saccharide (c) which rapidly generates an organic acid by the action of enterobacteria in the lower part of the gastrointestinal tract, the composition being coated with an enteric coating polymer material (d). In the composition, the saccharide (c) can be used either as a mixture with the drug (b) or as a coating layer on the drug (b). The latter composition includes an embodiment in which the polymer material (a)-coated drug (b) is coated with the saccharide (c), an embodiment in which the saccharide (c)-coated drug (b) is coated with the polymer material (a), and an embodiment in which the drug (b) is coated with the saccharide (c) and the polymer material (a).

More specifically, the present invention relates to the following compositions.

1) A colon-specific drug release oral composition in which a drug (b) and a saccharide (c) which rapidly generates an organic acid by the action of enterobacteria in the lower part of the gastrointestinal tract are coated with an organic acid-soluble polymer material (a), and the coating polymer material (a) is further coated with an enteric coating polymer material (d).

2) A colon-specific drug release oral composition in which a drug (b) is coated with an organic acid-soluble polymer material (a), the coated drug (b) is further coated with a saccharide (c) which rapidly generates an organic acid by the action of enterobacteria in the lower part of the gastrointestinal tract, and the coating saccharide (c) is further coated with an enteric coating polymer material (d).

3) A colon-specific drug release oral composition in which a drug (b) is coated with a saccharide (c) which rapidly generates an organic acid by the action of enterobacteria in the lower part of the gastrointestinal tract, the coated drug (b) is further coated with an organic acid-soluble polymer material (a), the coating polymer material (a) is further coated with an enteric coating polymer material (d).

4) A colon-specific drug release oral- composition in which a drug (b) is coated with an organic acid-soluble polymer material (a) and a saccharide (c) which rapidly generates an organic acid by the action of enterobacteria in the lower part of the gastrointestinal tract, and the coated drug (b) is further coated with an enteric coating polymer material (d).

The present invention also relates to a composition according to an embodiment in which separate compositions according to the above-described system are administered as a single preparation, and more particularly to a colon-specific drug release oral composition, which comprises a composition comprising a drug (b) coated with an organic acid-soluble polymer material (a) and a saccharide (c) which rapidly generates an organic acid by the action of enterobacteria in the lower part of the gastrointestinal tract and which may optionally be coated with an organic acid-soluble polymer material (a), the composition being further coated with an enteric coating polymer material (d).

The invention further relates to a colon-specific drug release oral composition, which comprises a composition comprising a drug (b) coated with an organic acid-soluble polymer material (a) and a saccharide (c) which rapidly generates an organic acid by the action of enterobacteria and which may optionally be coated with a water-insoluble release-controlling material (e), the composition being coated with a water-insoluble release-controlling material (e) and optionally with a hole-making material (f) and further coated with an enteric coating polymer material (d). In this composition, a coating layer comprising a water-permeable release-controlling material (e) (optionally with coexistence with a hole-making material (f)) is optionally provided on the inner side of the coating layer comprising an enteric coating polymer material (d) so as to increase the efficiency of organic acid generation by the action of enterobacteria, dissolution of the polymer material (a), and release of the drug (b). Provision of the coating layer (e) on the inside of the coating layer (d) is applicable to any composition of the present invention.

The present invention furthermore relates to a method for releasing a drug specifically in the colon of the gastrointestinal tract, more particularly to a method for releasing a drug specifically in the colon of the gastrointestinal tract, which comprises coating a composition comprising a drug (b) coated with an organic acid-soluble polymer material (a) and a saccharide (c) which rapidly generates an organic acid by the action of enterobacteria in the lower part of the gastrointestinal tract with an enteric coating polymer material (d).

The present invention will now be illustrated in more detail.

The basic concept of the colon-specific drug release system of the present invention is diagrammatically explained by referring to FIG. 1.

The system of the present invention consists of (1) a unit comprising an organic acid-generating saccharide (c) and (2) a unit comprising a drug (b) coated with an organic acid soluble polymer substance (a), which are further coated with an enteric coating polymer material (d), I.e., a polymer material which is not dissolved in the stomach but in the small intestine. If desired, a saccharide (c) which is degraded and generates an organic acid by the action of enterobacteria may be coated with an enteric coating polymer material. When orally administered to humans or mammals simultaneously, these two units pass the stomach almost unaffectedly and reaches the small intestine since the pH in the stomach is generally 6 or lower. In the small intestine having a pH of 6 to 7, the outermost coating layer which dissolves at pH 6 or higher, i.e., the coating layer made of the enteric coating polymer material (d) dissolves. Since the drug (b) in the unit (2) is protected by an inner coating layer which dissolves at a pH lower than 6, i.e., the coating layer made of the organic acid-soluble polymer material (a), the drug is not released in the small intestine. On the other hand, a saccharide (c) which is degraded and generates an organic acid by the action of enterobacteria and which is a component of the unit (1), dissolves in the small intestine. The saccharide (c) thus dissolved moves from the ileum, to the cecum, and then to the colon, it undergoes degradation by the action of drastically increasing enterobacteria to generate an organic acid. With respect to the unit containing the drug (b), the organic acid thus produced dissolves the membrane which dissolves at a pH of lower than 6, i.e., the organic acid-soluble polymer material (a), whereby the drug (b) is released specifically in the colon.

That is, the present invention provides a colon-specific drug release system characterized in that it specifically and rapidly releases a drug in the colon and that it comprises a combination of a saccharide (c) which generates an organic acid on decomposition by enterobacteria in the lower part of the gastrointestinal tract, a polymer material (a) which is dissolved by an organic acid, i.e., at a pH of lower than 6, an enteric coating polymer material (d), i.e., a polymer material which is dissolved at a pH of 6 or higher, and a drug (b).

The saccharide (c) used in the present invention, which is degraded by enterobacteria in the lower part of the gastrointestinal tract to generate an organic acid, is not limited by whether it is a monosaccharide or a polysaccharide as long as it is rapidly degraded by enterobacteria to generate an organic acid. Di- or polysaccharides which are not degraded by digestive enzymes in the gastrointestinal tract or not absorbed directly from the gastrointestinal tract are preferred. It is preferable for the saccharide which rapidly generates an organic acid to be rapidly dissolved and degraded to generate an organic acid. Accordingly) those having high water solubility are preferred. Specifically, the amount of water which is required to dissolve a 1 g portion of saccharides is preferably less than 5 ml, that is, saccharides having a water solubility of higher than 20 weight (w) I volume (v) % are preferred. Examples of such saccharides include lactulose, raffinose, cellobiose, stachyose, and fructooligosaccharides (which are synthetic disaccharides which show a high rate of degradation by enterobacteria). The fructooligosaccharides preferably include lactosucrose, such as Nyuka Oligo LS-55p (Hayashibara Syoji K.K.).

Saccharides which are degraded by digestive enzymes or directly absorbed from the gastrointestinal tract are also employable similarly to the above-described lactulose, etc., if coated with an enteric coating polymer material (d) which does not dissolve in the stomach but in the small intestine.

In order to deliver this type of saccharides to the lower part of the gastrointestinal tract more efficiently, it is preferable that the saccharide be previously coated with an organic acid-soluble polymer material (a) and then coated with an enteric coating polymer material (d). Examples of saccharides of this type are sucrose, glucose, xylose, fructose, maltose, and galactose.

As noted above, bacteria which live within the body are abundant in the oral cavity, rare in the stomach due to the acidicity, and also scarce in the upper part of the small intestine. Enterobacteria are increasing dramatically in the order of the ileum, the cecum, and the colon. A remarkable feature observed is an increase of anaerobic bacteria. In humans, Bacteroidaceae, *Bifidobacterium sp., Eubacterium sp., Clostridium sp.,* and Peptococcaceae constitute main microbial flora, and *Enterobacteriaceae sp., Streptococcus sp., Lactobacillus sp.,* and *Veillonella* sp. are detected next. The intestinal microbial flora does not so change within a healthy individual but varies among individuals or with stress, a diet or a disease. The variation is limited to specific bacteria and is not so large that all the microbial flora contributing to degradation of saccharides cannot be detected. While the bacteria absorb and metabolize saccharides, various organic acids are generated. The organic acids generated mainly include acetic acid, propionic acid, and butyric acid, while varying according to the saccharide. These organic acids are absorbed from the intestinal tract and become an energy source for humans or animals.

In the present system, the enteric coating polymer material (d) (a polymer material that dissolves at pH 6 or higher) dissolves in the vicinity of the duodenum, and enterobacteria enter the inside of the preparation together with water. The organic acid-generating saccharide (c) dissolves in water, and the enterobacteria degrade the saccharide to generate an organic acid. The pH thus decreases, and the organic acid-soluble polymer material (a) (a polymer material that dissolves at pH lower than 6) dissolves. As water enters, the saccharide (c) exudes and undergoes degradation by the action of the enterobacteria. If the enteric coating polymer material (d) is solely used, the organic acid-generating saccharide (c) may dissolve and diffuse and there is a fear that the organic acid generated does not produce sufficient effects as expected. It is recommended therefore that a composition containing the organic acid-generating saccharide (c) and a drug (b) is coated with the organic acid-soluble polymer material (a) or a composition comprising a drug (b) coated with the polymer material (a) and the organic acid-generating saccharide (c) are coated with a water permeable release-controlling material (e). If the water permeability is insufficient, the saccharide cannot dissolve sufficiently, and organic acid generation is retarded, tending to fail to manifest sufficient effects. In order to accelerate dissolution of the saccharide, the water permeable release-controlling layer (e) may contain a hole-making material (f), or the organic acid-soluble polymer material (a) may contain a substance having higher water permeability than the polymer material (a), i.e., the water permeable material (e). Where the organic acid-generating material (c) is present between the coating layer of the organic acid-soluble polymer material (a) and the coating layer of the enteric coating polymer material (d), the preparations include an embodiment in which the organic acid-generating saccharide (c) is coated with the organic acid-soluble polymer material (a) and may optionally be further coated with a water permeable release-controlling material (e) and an embodiment in which a composition containing the organic acid-generating saccharide (c) and the organic acid-soluble polymer material (a) is coated.

The saccharide for use in the present invention, for example, lactulose that is a synthetic disaccharide, is degraded by enterobacteria mainly comprising *Bifidobacterlum, Lactobacillus,* and Streptococcus in the lower part of the gastrointestinal tract, i.e., the colon to produce lactic acid, acetic acid, etc. Diabetics show a slight reduction in Bifidobacterium and Streptococcus, but such does not seem to have large influence on the degradation of lactulose because no change is observed in Lactobacillus. Raffinose, cellobiose, stachyose, maltose, and fructooligosaccharides are rapidly degraded by the main microbial flora in the colon similarly to lactulose, while there are slight differences in enterobacteria by which they are degraded.

Accordingly, it is considered that their degradation is not subject to large variation with slight variation of the microbial flora. The same seems to apply to sucrose, glucose, xylose, fructose, maltose, and galactose.

The organic acid which is generated by the action of enterobacteria serves to intentionally decrease the pH to dissolve the inner coating layer of the polymer material (a) and also to contribute to improvement in drug absorption.

The amount of the saccharide which is degraded by enterobacterial to generate an organic acid to be used in the present invention is not particularly limited as long as it is in the range for general use as excipients of preparations. A suitable amount is 1 to 99.9%, preferably 5 to 99.9%, and still more preferably 10 to 99.9%.

The organic acid-soluble polymer material (a), which is used in the present invention, is not particularly limited as far as it is pharmaceutically acceptable. Polymer materials which dissolve at pH lower than 6 are preferable, and those which dissolve at pH 5.5 or lower are more preferable. Specific examples of such polymer materials include a dimethylaminoethyl methacrylate-methyl methacrylate-butyl methacrylate copolymer (product name: Eudragit E), polyvinyl acetal diethylaminoacetate (product name: AEA, by Sankyo Co., Ltd.), and chitosan. If desired, the polymer material (a) may contain a water permeable release-controlling material (e). While not limiting as long as being pharmaceutically acceptable, examples of the water permeable release-controlling material include a copolymer of ethyl acrylate, methyl methacrylate, and trimethylammonioethyl methacrylate chloride (product name: Eudragit RS, produced by Röhm & Haas Co.), ethyl cellulose (product name: Ethocel, produced by Dow Chemical Co., Ltd.), hydroxypropylmethylcellulose (product names TC-5, produced by Shin-Etsu Chemical Co., Ltd.), hydroxypropylcellulose (product name: HPC, produced by Nippon Soda Co., Ltd.), polyethylene oxide, and polyvinylpyrrolidone. These materials may be used either individually or as an appropriate mixture thereof. If desired, it may contain a plasticizer. While not limiting as long as being pharmaceutically acceptable, the plasticizer includes triacetin, Macrogol 400, triethyl citrate, Tween 80, and castor oil, etc.

The water-insoluble and water-permeable release-controlling material (e) serves as a protecting layer for controlling the release of the organic acid-generating saccharide (c) from tablets or granules containing the same or for preventing diffusion of the tablets or granules contained therein. In this case, this layer may be provided between the coating layer of the organic acid-soluble polymer material (a) and the coating layer of the enteric coating polymer material (d).

The hole-making material (f) is used for acceleration of water permeation or for making holes through which entercobacteria can pass sufficiently in the release-controlling membrane. The hole-making material is not particularly limited as long as it is water-soluble and has a particle size greater than the size of enterobacteria (about 4 $\mu$m) when laminated. Salts (e.g., NaCl) and easily water-soluble saccharides (e.g., glucose) are preferred.

The coating amount of the organic acid-soluble polymer material (a) to be used is not particularly limited as long as it is within the range for general use as a polymer material in pharmaceutical preparations. Such an amount is usually 1 to 50%, preferably 2.5 to 40%.

The enteric coating polymer material (d), i.e., the polymer material which does not dissolve in the stomach but in the small intestine, is not particularly limited as far as it is pharmaceutically acceptable. Polymer materials which dissolve at pH 6 or higher are preferred. Examples thereof include methyl methacrylate-methacrylic acid (1:1) copolymer (product name: Eudragit L, produced by Röhm & Haas Co.), a methyl methacrylate-methacrylic acid (2:1) copolymer (product name: Eudrogit S, produced by Röhm & Haas Co.), an ethyl acrylate-methacrylic acid (1:1) copolymer (product name: Eudragit LD-55, produced by Röhm & Haas Co.), hydroxypropylmethylcellulosephthalate (JPXII), cellulose acetate phthalate (JPXII), and shellac (JPXII). These materials may be used either individually or as an appropriate mixture thereof. If desired, the enteric coating polymer material (d) may contain a plasticizer. Useful plasticizers include triacetin, Macrogol 400, triethyl citrate, Tween 80, and castor oil, etc.

The term "the lower part of the gastrointestinal tract" as used herein means the part from the ileum to the colon. The term "colon" as used herein means the part of the large intestine of from the cecum to the rectum. The "cecum" is a cecal pouch from which the large intestine starts and at one side of which the ileum is open.

The term "the upper part of the gastrointestinal tract" as used herein means the part from the stomach to the duodenum, inclusive of the jejunum.

The drug (b) which can be used in the present invention is not particularly limited.

Representative drugs which can be used effectively as a main active ingredient of the preparation include various polypeptides, proteins and derivatives thereof which are easily degraded in the upper part of the gastrointestinal tract and are absorbed in the lower part of the gastrointestinal tract to exhibit pharmacological activities. Examples of the drugs include insulin, calcitonin, angiotensin, vasopressin, desmopressin, LH-RH (luteinizing hormone-releasing hormone), somatostatin, glucagon, oxytocin, gastrin, ciclosporin, somatomedin, secretin, h-ANP (human artial natriuretic peptide), ACTH (adrenocorticotropic hormone), MSH (melanocyte-stimulating hormone), β-endorphin, muramyl dipeptide, enkephalin, neurotensin, bombesin, VIP (vasoacive intestinal polypeptide), CCK-8 (cholecystokinin-8), PTH (parathyroid hormone), CGRP (calcitonin gene-related peptide), TRH (thyrotropin-releasing hormone), endocerine, hGH (human growth hormone), cytokines (e.g., interleukin, interferon, colony-stimulating factor, and tumor necrosis factor), as well as derivatives thereof.

The above peptides and proteins include not only naturally occurring substances but pharmacologically active derivatives thereof and analogues thereof. For example, calcitonin used in the present invention includes not only naturally occurring products, such as salmon calcitonin, human calcitonin, porcine calcitonin, eel calcitonin, and fowl calcitonin, and also includes analogues, such as [Asul, 7]-eel calcitonin (Elcatonin). Further, insulin includes human insulin, porcine insulin, bovine insulin as well as their analogues, such as recombinants.

Drugs effective on diseases of the lower part of the gastrointestinal tract, such as Crohn disease, ulcerative colitis, irritable colitis, and colic cancer, are also useful in the present invention. Examples of such drugs include salazosulfapyridine, 5-aminosalicylic acid, cortisone acetate, triamcinolone, dexamethasone, budesonide, tegafur, fluorouracil, and derivatives thereof.

In addition to these physiologically active substances, other various physiologically active substances can be used as a main active ingredient that is absorbed efficiently from the lower part of the gastrointestinal tract. For example, antitussive expectorants, such as theophylline; vasodilators, such as nicardipine hydrochloride and nifedipine; coronary vasodilators, such as isosorbide nitrite; antipyretic analgesics, such as acetaminophen, indomethacin, hydrocortisone, ibuprofen, and salazopyrin can be used.

In order to make these drugs easily absorbable in the colon, it is possible to add one or more pharmaceutically acceptable additives to the drug. Suitable additives include surface active agents, such as sucrose fatty acid esters (e.g., Sugar Ester L1695, produced by Mitsubishi Chemical Foods Co., Ltd.), sodium laurylsulfate, polyoxyethylene hydrogenated castor oil (e.g., HCO-60), and polyoxyethylene sorbitan higher fatty acid esters (e.g., Tween 80); cholic acids and salts thereof, such as sodium glycocholate and chenodeoxycholic acid; organic acids and salts thereofi such as citric acid, tartaric acid, benzoic acid, and capric acid; dissolution aids, such as β-cyclodextrin; pH adjusters, such as sodium citrate, meglumine, and MgO; trypsin inhibitors, such as camostat mesilate; enzyme inhibitors, such as aprotinin; antiinflammatory agents, such as salicylic acid, aspirin, sodium dichlofenac; aromas, such as peppermint oil; and antibiotics, such as bacitracin and amphotericin B.

Without depending on whether a drug is acidic or basic, it is possible to adjust the pH of the system at the time when tablets dissolve, by using an organic acid or a basic substance. The organic acids include citric acid and tartaric acid, and the basic substances include solid bases (e.g., MgO), basic amino-sugars (e.g., meglumine), and basic amino acids (e.g., lysine and arginine).

Where a drug has low solubility at pH 6 or lower dissolution aids can be added. The dissolution aid is not limited as long as it is pharmaceutically acceptable. Examples include nonionic surface active agents, such as sucrose fatty acid esters, glycerol fatty acid esters, sorbitan fatty acid esters (e.g., sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g., chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

For the purpose of controlling the drug release from tablets, water-soluble polymers, such as polyethylene oxide, hydroxypropylcellulose, hydroxypropylmethylcellulose, and polyvinylpyrrolidone, may be added.

In addition, pharmaceutically acceptable excipients, such as stabilizers and bulking agents, may also be added.

The kind of these additives may be altered according to the drug.

The colon-specific drug release system of the present invention is a preparation comprising, as basic constituents, a saccharide (c) which is degraded by enterobacteria to generate an organic acid, a polymer material (a) which is dissolved by an organic acid generated on degradation of the saccharide by the action of enterobacteria, and an enteric coating polymer material (d). The preparation may have any dosage form, such as tablets, granules, fine granules, powders, and capsules.

The constitution of the present invention will further be explained by referring to the embodiments shown in the accompanying drawings, but the present invention is not deemed to be limited thereto.

The preparation shown in FIG. 2-A comprises a drug (b)-containing tablet or granule coated with an organic acid-soluble polymer material (a) (i.e., a polymer material which dissolves at pH lower than 6) and a saccharide (c)-containing tablet or granule coated with an enteric coating polymer material (d) (i.e., a polymer material which does not dissolve in the stomach but in the small intestine, namely, a polymer material which dissolves at pH 6 or higher), both the two coated tablets (or granules) being pressed into a tablet or put in a capsule, together with a excipient, and the tablet or capsule being further coated with at enteric coating polymer material (d).

The preparation shown in FIG. 2-B comprises a drug (b)-containing tablet or granule coated with an organic acid-soluble polymer material (a) (i.e., a polymer material which dissolves at pH lower than 6) and a saccharide (c)-containing tablet or granule coated with a water-insoluble release-controlling material (e), both the coated tablet (or granule) being pressed into a tablet or put in a capsule, together with a excipient, the coated tablet or capsule being further coated with a water-insoluble release-controlling material (e) containing a hole-making material (f), and further coated with an enteric coating polymer material (a material dissolving at pH 6 or higher).

The preparation shown in FIG. 2-C comprises a drug (b)-containing tablet or granule coated with an organic acid-soluble polymer material (a) (i.e., a polymer material which dissolves at pH lower than 6), which is coated with a saccharide (c) using an appropriate additive, the saccharide (c) being coated with a water-insoluble release-controlling material (e), and further coated with an enteric coating polymer material (d) (i.e., a polymer material dissolving at pH 6 or higher).

The preparations described above are in accordance with the principle of the drug release system of the present invention. Applied preparations according to the system are now explained below by referring to FIG. 2.

The preparation shown in FIG. 2-D is easy to produce and seems more suitable for industrialization to achieve high productivity. That is, a composition comprising a drug (b) and a saccharide (c) which is degraded by enterobacteria to generate an organic acid (for example, tablets, granules, fine granules, or powders) is coated first-with a polymer material (a) which is dissolved by an organic acid generated on degradation of the saccharide by the action of enterobacteria, and then coated with an enteric coating polymer material (d) (dissolving in the small intestine but not in the stomach). A material permeable to water may be added to the organic acid-soluble polymer material (a) in forming a layer, or a layer of a material permeable to water (water-soluble layer) may be provided between the layer of the enteric coating polymer material (d) (dissolving at pH 6 or higher) and the layer of the organic acid-soluble polymer material (a) (dissolving at pH lower than 6), so as to sandwich the water-soluble membrane. The resulting preparation in the form of tablets, granules, fine granules, powders, etc. can be administered either as such or charged in water-soluble capsules to humans or mammals, and the preparation passes the stomach almost unaffectedly and reaches the small intestine since the pH in the stomach is generally 6 or lower. While the water-soluble capsules are dissolved in the stomach, the inside preparation moves to the small intestine almost unaffectedly. In the small intestine having a pH of 6 to 7, the outermost coating layer which dissolves at pH 6 or higher, i.e., the coating layer made of the enteric coating polymer material (d) dissolves. Since the tablet (or granule, etc.) is still protected by an inner coating layer which dissolves at pH lower than 6, i.e., the coating layer made of the organic acid-soluble polymer material (a), the drug is not released in the small intestine. Therefore, the preparation also passes through the small intestine without releasing the drug (b) until it reaches the colon. Then, the polymer material (a) dissolving at pH lower than 6 is dissolved in the colon to release the drug (b) if the colon inclusive of the cecum has a pH of lower than 6 or can be adjusted intentionally to a pH of lower than 6.

INDUSTRIAL APPLICABILITY

Experiments and their results are hereinafter shown for demonstrating the excellent effects of the system and preparations according to the present invention.

It was verified that the organic acid-soluble polymer material (a), among the polymer materials used as coating materials in the preparations of the present invention, is dissolved in the cecum, the colon, etc. to release a drug. First of all, because the cecum or the colon is likely to change their pH values with diets (see Test Example 1), an attempt was made to change the pH artificially. Lactulose (100 mg/animal), which is a synthetic disaccharide and is degraded by enterobacteria specifically and rapidly (see Test Example 2), was administered to rats, and the pH in the cecum was measured with time. The pH was reduced to about 5.5 in 3 to 4 hours from the administration of lactulose, and the pH reduction lasted for 8 hours (see Test Example 3). Sulfisoxazole was coated with Eudragit E that dissolves at pH lower than 6 and further coated with an enteric coating material Eudragit L. The resulting Sulfisoxazole preparation was administered to rats with or without 200 mg/rat of lactulose. As a result, the drug appeared in the plasma after 6 hours from the administration in the lactulose-administered group, whereas no drug was detected from the plasma of the group no lactulose-administered group, thus showing the effect of lactulose (see Test Example 4). Another experiment revealed that the time required for a preparation to move through the gastrointestinal tract to reach the cecum is from 4 to 8 hours. It can thus be understood that the drug release took place in the cecum.

The preparation shown in FIG. 2-B was also proved to release its drug in the cecum in about 5 hours from the administration (see Test Example 5).

TEST EXAMPLE 1

The pH of the cecum of rats fed on meat feed ad libitum was found to range from 7.2 to 8.2, which is higher than pH 5.0 to 5.6 in rats in fed condition. These results indicate liability to great pH variation in the cecum with diets.

TEST EXAMPLE 2

A 1/15 M phosphate buffer solution ($NaH_2PO_4$-$Na_2HPO_4$; pH 7.3; hereinafter referred to as PBS) was made isotonic by addition of sodium chloride and adjusted to pH 6.8 by $CO_2$ bubbling. The contents of the cecum of an SD male rat was dispersed therein to prepare a 10 w/v % dispersion of the cecal contents in PBS (hereinafter referred to as C-PBS). To 10 ml of C-PBS was added 100 mg of lactulose, and the mixture was shaken (50 strokes/min) at 37° C. under an anaerobic condition, and the pH change was measured. As a control, the same test was conducted on no lactulose-administered C-PBS.

As shown in the table, it was proved that lactulose undergoes fermentation in the cecal contents to generate an organic acid thereby reducing the pH.

| Lactulose | Time (hr) | | | | | |
| --- | --- | --- | --- | --- | --- | --- |
| (mg) | 0 | 2 | 4 | 6 | 8 | 24 |
| 0 | 6.42 | 6.20 | 6.17 | 6.15 | 6.12 | 6.02 |
| 100 | 6.42 | 5.93 | 5.64 | 5.41 | 5.27 | 4.76 |

The same test was carried out on a mixture of 30 w/v % C-PBS and lactulose. As shown in the table, the pH of the cecal contents rapidly decreases by the addition of lactulose.

| Time (hr) | 0 | 2 | 4 | 6 | 8 |
| --- | --- | --- | --- | --- | --- |
| pH | 6.42 | 5.39 | 5.25 | 5.15 | 5.08 |

TEST EXAMPLE 3

SD male rats deprived of food overnight were orally given a lactulose aqueous solution (100 mg/rat), and the pH in the cecum was measured with time. As shown in the table, it was verified that lactulose ferments in the cecum in vivo to reduce the pH significantly.

| Time (hr) | 0 | 1 | 2 | 3 | 4 | 5 | 6 | 7 |
| --- | --- | --- | --- | --- | --- | --- | --- | --- |
| pH | 7.6 | 8.2 | 6.8 | 6.2 | 5.5 | 5.6 | 5.8 | 5.3 |

TEST EXAMPLE 4

Sulfisoxazole (SIZ) and PEG 4000 were mixed at a rate of 1:3, and capsules made of Eudragit E100 (thickness: 0.25 mm) were filled with the mixture (20 mg/capsule; SIZ content: 5 mg). A methanol solution of Eudragit L100/castor oil (5/1) (10 w/v %) was applied to the capsules by the dipping method to give a solids coating of 17 wt %. The resulting preparation (SIZ-CDS) was subjected to an elution test according to the paddle method (37° C., 100 rpm) specified in The Japanese Pharmacopeia (hereinafter, referred to as JP) in 1st fluid for 4 hours and then in 2nd fluid for 4 hours. As a result, the drug was not released during the testing.

The SIZ-CDS preparation was orally administered to SD male rats (8-week-old) deprived of food for 20 hours together with 1 ml of a lactulose aqueous solution (lactulose: 200 mg), and the sulfisoxazole concentration in plasma was determined with time. In a control group, the same preparation was given together with 1 ml of water. For comparison, 20 mg/capsule of SIZ/PEG 4000 (⅓) was put in gelatin capsules, and the capsules were coated with Eudragit L100/castor oil (5/1) to prepare an enteric preparation (SIZ-ENT). The SIZ-ENT was orally administered to the rats together with 1 ml of a lactulose aqueous solution (lactulose: 200 mg), and blood was taken from the carotid artery with time to determine the drug concentration in plasma by means of a Tsuda reagent.

As shown in FIG. 3, in the lactulose-administered group, the SIZ-CDS preparation shows a significant delay in releasing the drug as compared with the SIZ-ENT preparation, proving that the drug of the SIZ-CDS preparation is released in the lower part of the gastrointestinal tract. In the no lactulose-administered group, the drug was hardly detected in the plasma. Accordingly, it was shown that lactulose in SIZ-CDS ferments in the lower part of the gastrointestinal tract to generate an organic acid thereby decreasing the pH in that part whereby the Eudragit E100 dissolves to release the drug.

TEST EXAMPLE 5

A tablet comprising 100 mg of lactulose was coated with 10% of Eudragit RS100. The coated tablet releases lactulose in about 7 hours. Separately, a tablet containing a pigment Red #103 was coated with Eudragit E100. The two tablets were put in a capsule, and the capsule was coated with 10% of a dispersion of NaCl particles (24 mesh or greater) in a methanol solution of Eudragit RL100. On shaking the capsule in 1 w/v % C-PBS under an anaerobic condition, the pigment was released after 5 hours.

TEST EXAMPLE 6

The following solution was subcutaneously administered to beagle dogs in fasted condition. Blood was taken with time to determine the phosphorus concentration in plasma using Inorganic Phosphorus E-HA Test Wako (Wako Pure Chemical Industries, Ltd.).

1% Gelatin solution containing 50 IU/0.2 ml of salmon calcitonin (pH 3; 0.2 ml; 50 IU/animal)

As shown in FIG. 8, the phosphorus level in plasma increases with time in the control group (untreated), while it was suppressed when salmon calcitonin was given.

TEST EXAMPLE 7

An isotonic phosphate buffer solution (pH: 7.3; PBS) was adjusted to pH 6.8 by $CO_2$ bubbling. The contents of the cecum of a rat deprived of food for 24 hours was dispersed therein to prepare a 10 w/v % dispersion of the cecal contents in PBS (CPBS). To 20 ml of CPBS was added 200 mg of a saccharide, and the mixture was shaken in a water bath at 37° C., and the pH of the CPBS was measured with time.

As shown in FIG. 10, it was clarified that, under these conditions, maltose, glucose, fructose, fructooligosaccharide, sucrose, fructose, and galactose are degraded by enterobacteria to generate an organic acid similarly to lactulose.

The system of the present invention is designed to deliver a drug specifically to the colon, thereby making it possible to deliver the drug in a high concentration to an affected site in the large intestine while avoiding unfavorable side effects of the drug and also making it feasible to efficiently deliver those drugs which are absorbed satisfactorily through the large intestine.

As described in Examples and Test Examples, it has been verified that any of the drugs tested can be absorbed. Therefore, the present invention provides a preparation technique for general purposes regardless of the physical properties of drugs..

BRIEF DESCRIPTION OF THE DRAWINGS

In FIG. 1, (a) . . . organic acid-soluble polymer material; (b) . . . drug; (c) . . . saccharide which rapidly generates an organic acid by the action of enterobacteria in the lower part of the gastrointestinal tract; and (d) . . . enteric coating polymer material.

In FIG. 2, (a) . . . organic acid-soluble polymer material; (b) . . . drug; (c) . . . saccharide which rapidly generates an organic acid by the action of enterobacteria in the lower part of the gastrointestinal tract; (d) . . . enteric coating polymer material; (e) . . . water-insoluble release-controlling material; (f) . . . hole-making material; and (g) excipient.

FIG. 3 is a graph showing the change in drug concentration in plasma with time in rats of the group given the system of the present invention comprising an SIZ-CDS preparation containing sulfisoxazole and lactulose, the group given an enteric coating preparation (Comparative Example 1), and the group given a control system comprising the SIZ-CDS preparation and water (Test Example. 4).

FIG. 4 is a graph showing the change in drug release behavior (rate of release) with time from a colon-specific drug releasing composition of the present invention (Example 2) in an artificial intestinal juice organ artificial intestinal juice containing 1 w/v % of the cecal contents.

THE BEST MODE FOR CARRYING OUT THE INVENTION

Figure 1:
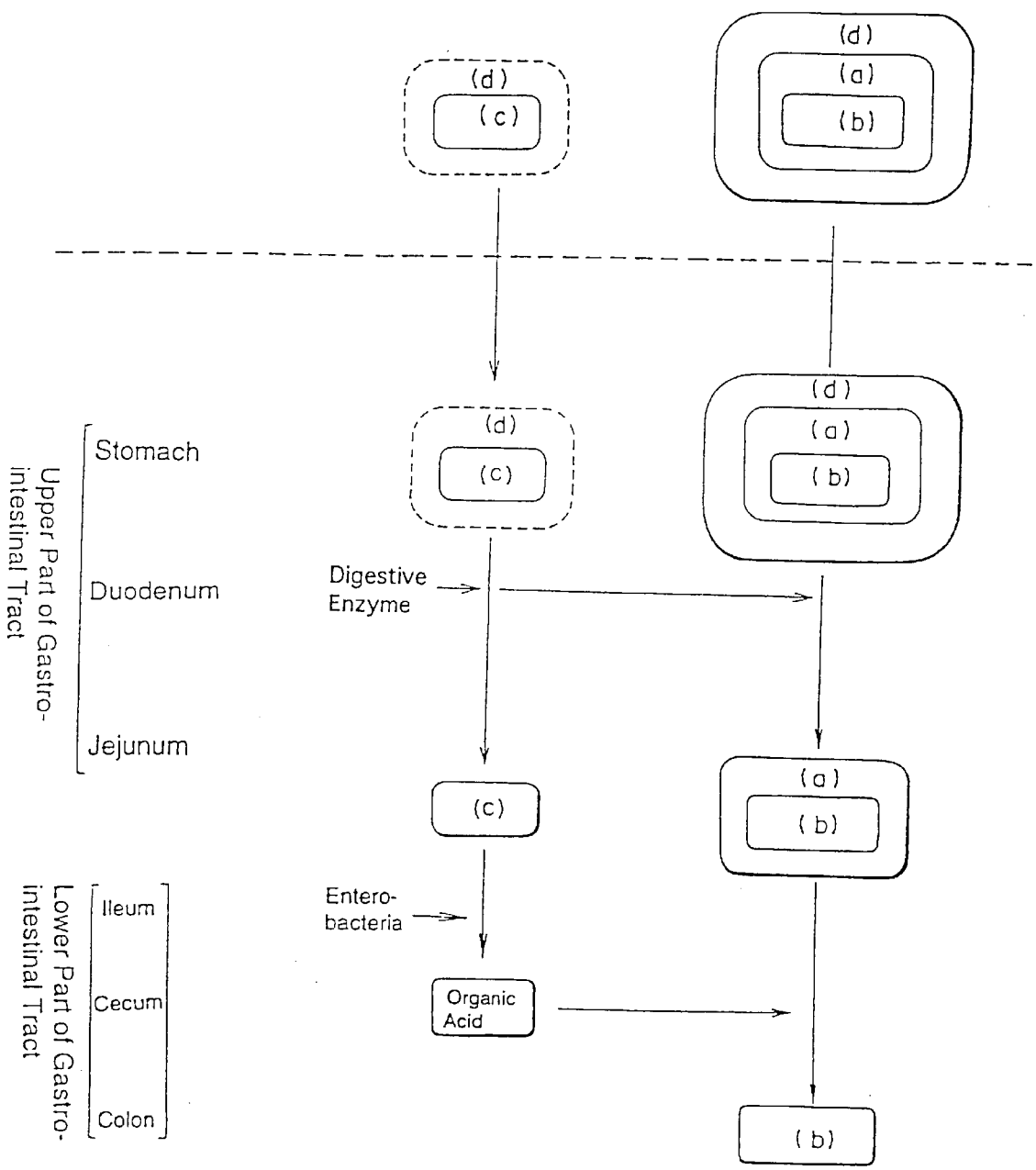
FIG. 1 is a diagram illustrating the mechanism of drug release in the colon according to the colon-specific drug release system of the present invention.
Figure 2:
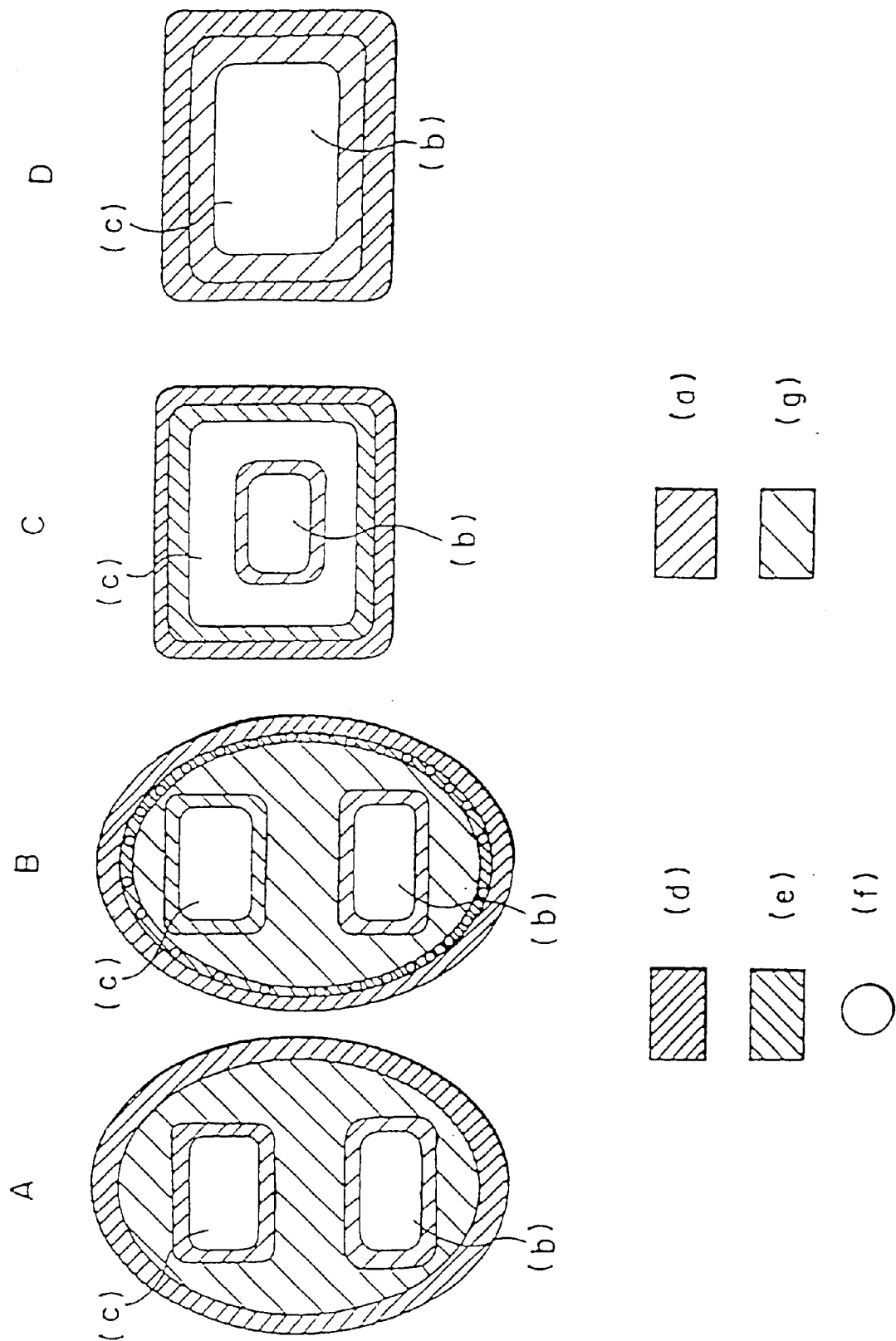
FIG. 2 shows examples of the colon-specific drug release system of the present invention.

The present invention will now be illustrated in greater detail with reference to Examples, but it should be understood that the present invention is not deemed to be limited thereto.

EXAMPLE 1

Tablets each weighing 150 mg and containing lactulose and 5% of a pigment (Red #103) were prepared. The tablets were coated at a varied ratio as shown in the following table, and the coated tablets were subjected to an elution test in JP 1st fluid and a 1 w/v % C-PBS. The drug release initiation time in C-PBS was shorter than that in JP 2nd fluid in every case.

| Membrane Composition | Coating Composition Ratio | Coating Amount (%) | Drug Release Initiation Time (hr) JP Second Fluids | Drug Release Initiation Time (hr) Cecum Content |
|---|---|---|---|---|
| Eudragit E100 | — | 7.5 | 20.0 | 1.5 |
| Eudragit E100/ | 9:1 | 7.5 | 10.5 | 1.0 |
| Eudragit RS100L | 9:1 | 15.0 | >23.0 | 2.0 |
|  | 9:1 | 20.0 | >24.0 | 2.5 |
|  | 7:3 | 15.0 | 6.0 | 2.5 |
|  | 7:3 | 20.0 | 6.67 | 1.8 |
| Eudragit E100/ | 9:1 | 7.5 | >24.0 | 1.67 |
| Eudragit RS100 | 7:3 | 7.5 | 21.5 | 1.2 |
|  | 7:3 | 10.0 | >24.0 | 3.0 |
|  | 7:3 | 20.0 | >24.0 | 4.25 |
|  | 5:5 | 7.5 | >24.0 | 1.33 |

EXAMPLE 2

| | |
|---|---|
| 5-Aminosalicylic acid (5-ASA) | 50.0 mg |
| Lactulose | 50.0 mg |
| MgO | 8.2 mg |
| Polyvinylpyrrolidone | 1.5 mg |
| Mannitol | 66.8 mg |
| Maltose | 3.5 mg |
| Total: | 180.0 mg |

5-Aminosalicylic acid (5-ASA), MgO for neutralization, lactulose, and other additives were mixed in a mortar and made to prepare tablets. The tablets were coated with 11 wt % of a 10 w/v % methanol solution of Eudragit L100/castor oil (5/1) by means of a vacuum air drying type coating pan (Hicoater Model HCT-30, manufactured by Freund Sangyo K.K.) to prepare enteric tablets. The enteric coating tablets were further coated with 11 wt % of a 10 w/v % methanol solution of Eudragit E100 and furthermore coated with 12 wt % of Eudragit L100/castor oil (5/1) to obtain a preparation of the present invention.

The results of the dissolution test in JP 2nd fluids and in a 1 w/v % dispersion of the cecal contents are shown in FIG. 4. The drug release initiation time in the 1 w/v % cecal contents was reduced to about ⅙ of that in JP 2nd fluids. As a result, the drug release from the preparation was accelerated by the action of enterobacteria. The rate of release in the cecal contents was higher than in JP 2nd fluids.

The preparation of the present invention was orally administered to beagle dogs (n=3, samples 1, 2 and 3) in fasted condition together with 30 ml of water. As a control, the enteric coating preparation was used. Blood was taken with time to determine the drug concentration in plasma by fluorescence-HPLC. As a result, the drug release of the preparation of the present invention is delayed as compared with the enteric coating preparation. The transit time of the small intestine in beagle dogs in fasted conditions is about 1 hour, and the time for reaching the colon is 2 to 3 hours in average, but are considerably influenced by the gastric emptying time. The appearance time of 5-aminosalicylic acid in plasma after oral administration of the preparation of the present invention is 3 hours and it delays for 1 hour or more compared to the enteric coating preparation. From these results, it was shown that the preparation of the present invention rapidly releases the drug in the lower part of the gastrointestinal tract.

EXAMPLE 3

| | |
|---|---|
| 5-Aminosalicylic acid | 100.0 mg |
| Lactulose | 50.0 mg |
| MgO | 16.4 mg |
| Actisol | 7.5 mg |
| Total: | 173.9 mg |

5-Aminosalicylic acid (5-ASA), MgO for neutralization, lactulose, and other additives were mixed in a mortar and made to prepare tablets. The tablets were coated with 11 wt % of a 10 w/v % methanol solution of Eudragit L100/castor oil (5/1) by means of a Hicoater to prepare enteric coating tablets. Further, the tablets were coated with 11 wt % of a 10 w/v % methanol solution of Eudragit E100 by means of a Hicoater and furthermore coated with 12 wt % of Eudragit L100/castor oil (5/1) to obtain the preparation of the present invention. The dissolution initiation time of the preparation of the present invention in JP 2nd fluid was 18 hours.

The preparation of the present invention was orally administered to beagle dogs in non-fasted condition (n=3) together with 30 ml of water. As a control, the enteric coating preparation was similarly administered. Blood was taken with time to determine the drug concentration in plasma by fluorescence-HPLC.

Figure 5:
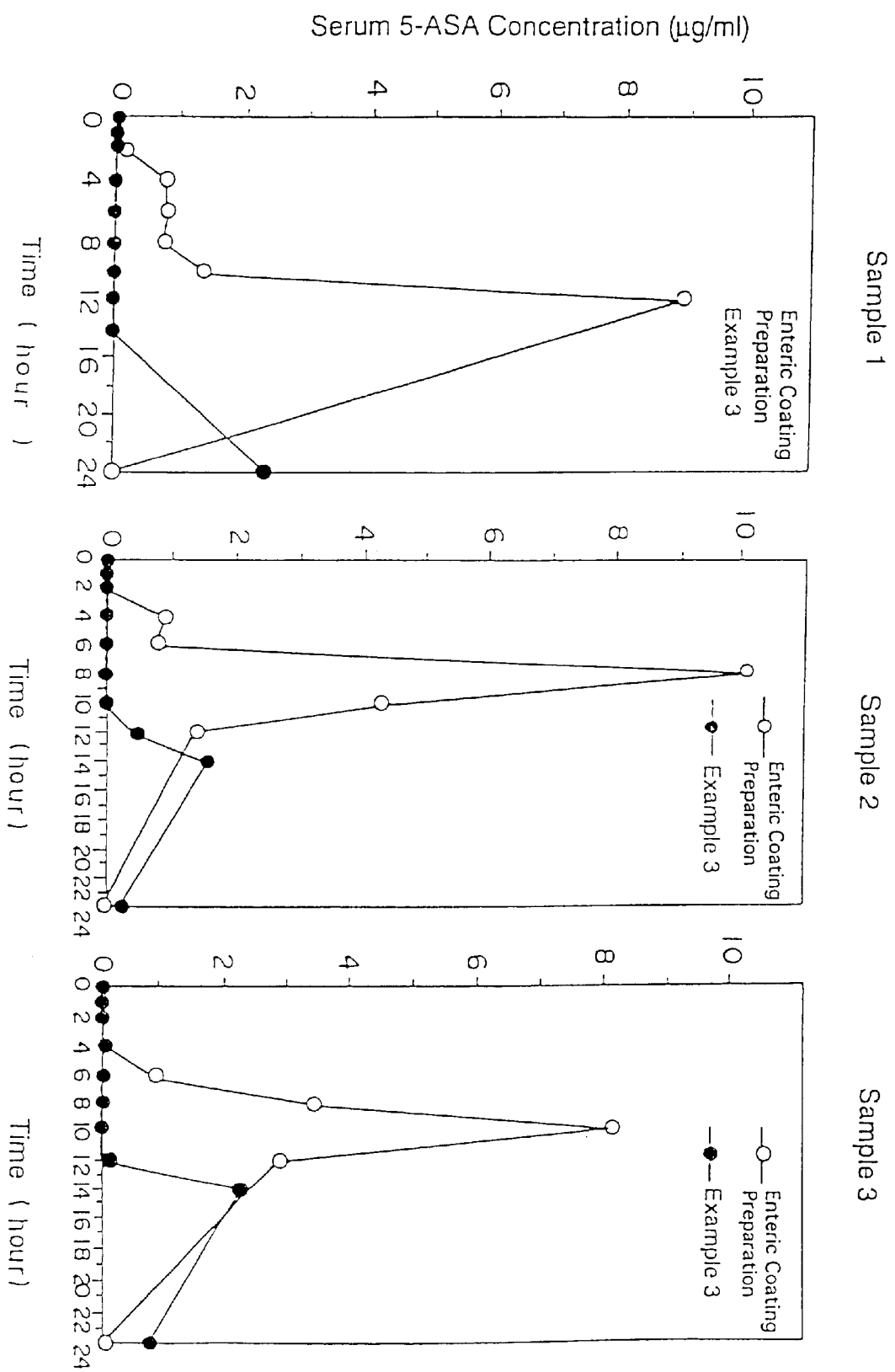
FIG. 5 is a graph showing the change in drug concentration in plasma as a function of time in beagle dogs in non-fasted condition having received a colon-specific drug releasing composition of the present invention containing 5-aminosalicylic acid (Example 3) or an enteric coating preparation.

As shown in FIG. 5, the preparation of the present invention is obviously delayed in drug release as compared with the enteric coating preparation. The small intestine transit time of the preparation in beagle dogs in non-fasted condition is about 1 hour. Therefore, it was shown that the preparation of the present invention releases its drug in the lower part of the gastrointestinal tract, even with the possible inter-variation of the gastric emptying time being taken into consideration.

EXAMPLE 4

| | |
|---|---|
| Sodium 5-aminosalicylate | 100.0 mg |
| Lactulose | 50.0 mg |
| Actisol | 7.5 mg |
| Total: | 157.5 mg |

Sodium 5-aminosalicylate, lactulose, and the additive were mixed in a mortar and made to prepare tablets. The tablets were coated with 11 wt % of a 10 w/v % methanol solution of Eudragit E100 by means of a Hicoater and further coated with 12 wt % of Eudragit L100/castor oil (5/1) to obtain the preparation of the present invention.

The results of a dissolution test in JP 2nd fluid and 1 w/v % of cecal contents revealed that the drug release initiation time of the preparation in the cecal contents was reduced to about ⅙ of that in JP 2nd fluid.

EXAMPLE 5

| Insulin | 10 mg |
|---|---|
| Lactulose | 100 mg |
| Meglumine | 30 mg |
| Citric acid | 10 mg |
| Glycocholate Na | 100 mg |
| Total: | 250 mg |

Insulin, lactulose, and other additives were mixed in a mortar and made to prepare tablets. The tablets were coated first with 11 wt % of Eudragit E100 and then with 11 wt % of Eudragit L100 castor oil (5/1) in the same manner as in Example 4 (by means of a Hicoater) to obtain the preparation of the present invention.

Two tablets of the preparation were orally administered to beagle dogs (n=3, samples 1, 2 and 3) in fasted condition together with 30 ml of water. Blood was taken with time to determine the glucose level in plasma by means of a glucose measurement kit.

Figure 6:
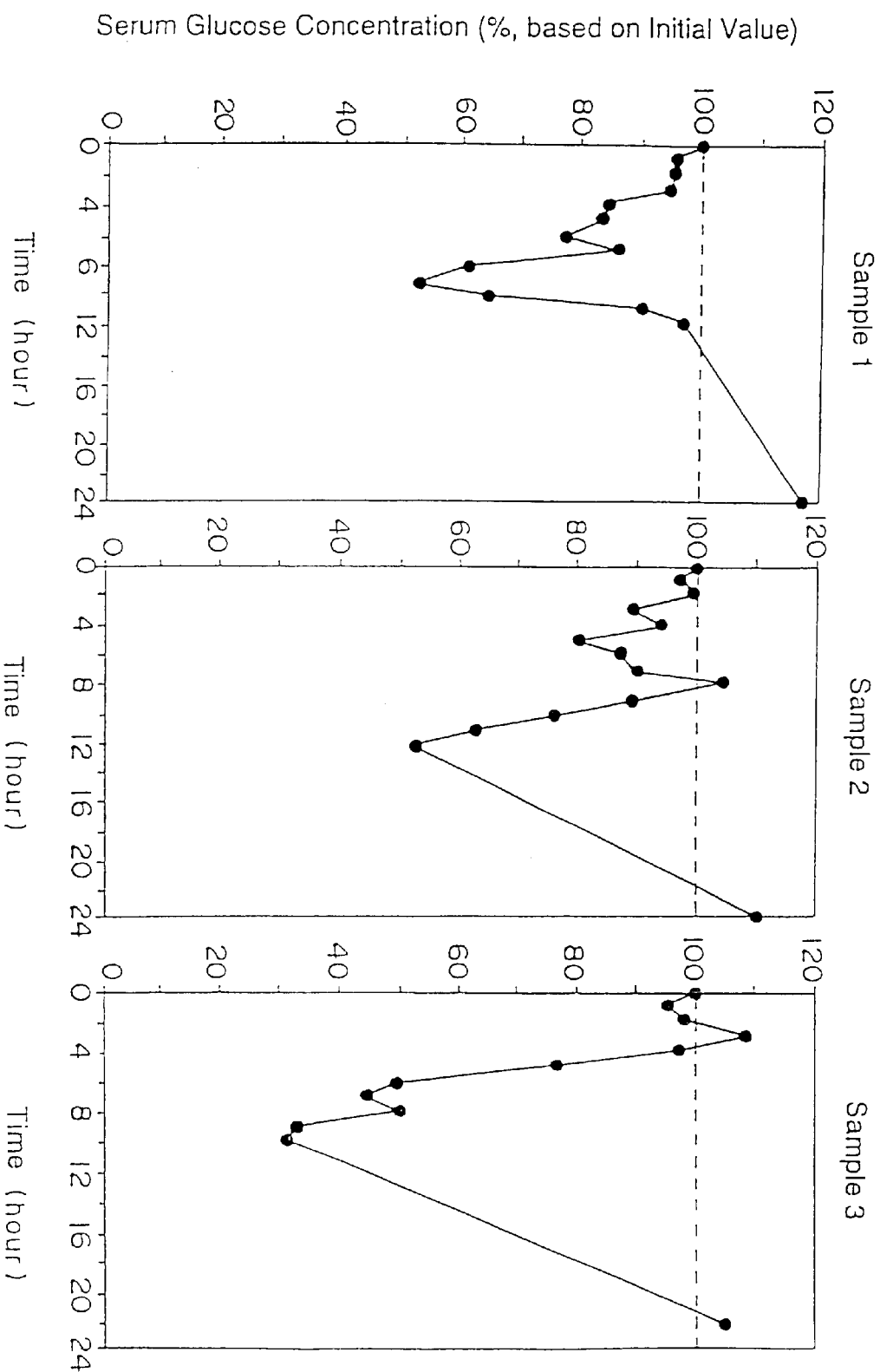
FIG. 6 is a graph showing the change in glucose level in plasma as a function of time in beagle dogs in fasted condition having received a colon-specific drug releasing composition of the present invention containing insulin (Example 5).

As shown in FIG. 6, a reduction in glucose level in plasma was observed from 4 or 5 hours after administration. Taking into consideration the time for the preparation to reach the colon in beagle dogs in fasted condition, it was revealed that the preparation of the present invention releases the drug in the lower part of the gastrointestinal tract whereby insulin can be absorbed.

EXAMPLE 6

| Insulin | 20 mg |
|---|---|
| Lactulose | 108 mg |
| Meglumine | 30 mg |
| Citric acid | 10 mg |
| Sodium laurylsulfate | 12 mg |
| Total: | 180 mg |

Insulin, lactulose, and other additives were mixed in a mortar and made to prepare tablets. The tablets were coated first with 11 wt % of Eudragit E100 and then with 11 wt % of Eudragit L100/castor oil (5/1) in the same manner as in Example 4 (by means of a Hicoater) to obtain the preparation of the present invention.

The resulting preparation was orally administered to beagle dogs in fasted condition together with 30 ml of water. Blood was taken with time to determine the glucose level in plasma by means of a glucose measurement kit.

As a result, a sustained reduction in plasma glucose level was observed.

EXAMPLE 7

| Tablet 1 | |
|---|---|
| 5-Aminosalicylic acid | 50.0 mg |
| MgO | 8.2 mg |
| Actisol | 5.7 mg |
| Total: | 63.9 mg |

| Tablet 2 | |
|---|---|
| Lactulose | 100 mg |

5-Aminosalicylic acid (5-ASA), MgO for neutralization, and the additive were mixed in a mortar and made to prepare tablets. The tablets were coated with 11 wt % of a 10 w/v % methanol solution of Eudragit E100 by means of-a Hicoater. Then tablets of lactulose were prepared and coated with 11 wt % of a 10 w/v % methanol solution of Eudragit L100/castor oil (5/1). Each one of the drug tablets and the lactulose tablets and 200 mg of lactose were put in a #1 gelatin capsule. The capsule was coated with 12 wt % of Eudragit L100/castor oil (5/1) to obtain the preparation of the present invention.

EXAMPLE 8

| Tablet 1 | |
|---|---|
| 5-Aminosalicylic acid | 50.0 mg |
| MgO | 8.2 mg |
| Actisol | 5.7 mg |
| Total: | 63.9 mg |

| Tablet 2 | |
|---|---|
| Lactulose | 100 mg |

5-Aminosalicylic acid (5-ASA), MgO for neutralization, and the additive were mixed in a mortar and made to prepare tablets. The tablets were coated with 11 wt % of a 10 w/v % methanol solution of Eudragit E100 by means of a Hicoater. Then tablets of lactulose were prepared and coated with 11 wt % of a 10 w/v % methanol solution of Eudragit RS100/triacetin (5/1). Each one of the tablets 1 and the tablets 2 and 200 mg of lactose were put in a #1 gelatin capsule. The capsule was coated first with a methanol dispersion of Eudragit RS100L/NaCl (particle size: 75 to 355 $\mu$m) (½) and then with 12 wt % of Eudragit L100/castor oil (5/1) to obtain the preparation of the present invention.

EXAMPLE 9

| Tablet | |
|---|---|
| 5-Aminosalicylic acid | 100.0 mg |
| MgO | 16.4 mg |

| Tablet | |
|---|---|
| Actisol | 5.7 mg |
| Total: | 122.1 mg |

5-Aminosalicylic acid (5-ASA), MgO for neutralization, and the additive were mixed in a mortar and made to prepare tablets. The tablets were coated with 11 wt % of a 10 w/v % methanol solution of Eudragit E100 by means of a Hicoater. The coated tablets were further subjected to powder coating with lactulose using a TC-5 solution as a binder to have 50 mg of lactulose per tablet. The lactulose-coated tablets were coated with 11 wt % of a 10 w/v % methanol solution of Eudragit RS100L/triacetin (5/1) by means of a Hicoater and further coated with 12 wt % of Eudragit L100/castor oil (5/1) to obtain a preparation of the present invention.

EXAMPLE 10

In the same manner as in Example 4, the tablets prepared in Example 5 were coated successively with 11 wt % of Eudragit E100/Eudragit RS100L (9/1), 1 wt % of TC5E, and 11 wt % of Eudragit L100/castor oil (5/1) in this order by means of a Hicoater to obtain a preparation of the present invention.

Two tablets of the preparation were orally administered to beagle dogs (n=3; samples 1, 2, and 3) in fasted condition together with 30 ml of water, and blood was taken with time to determine the glucose level in plasma.

Figure 7:
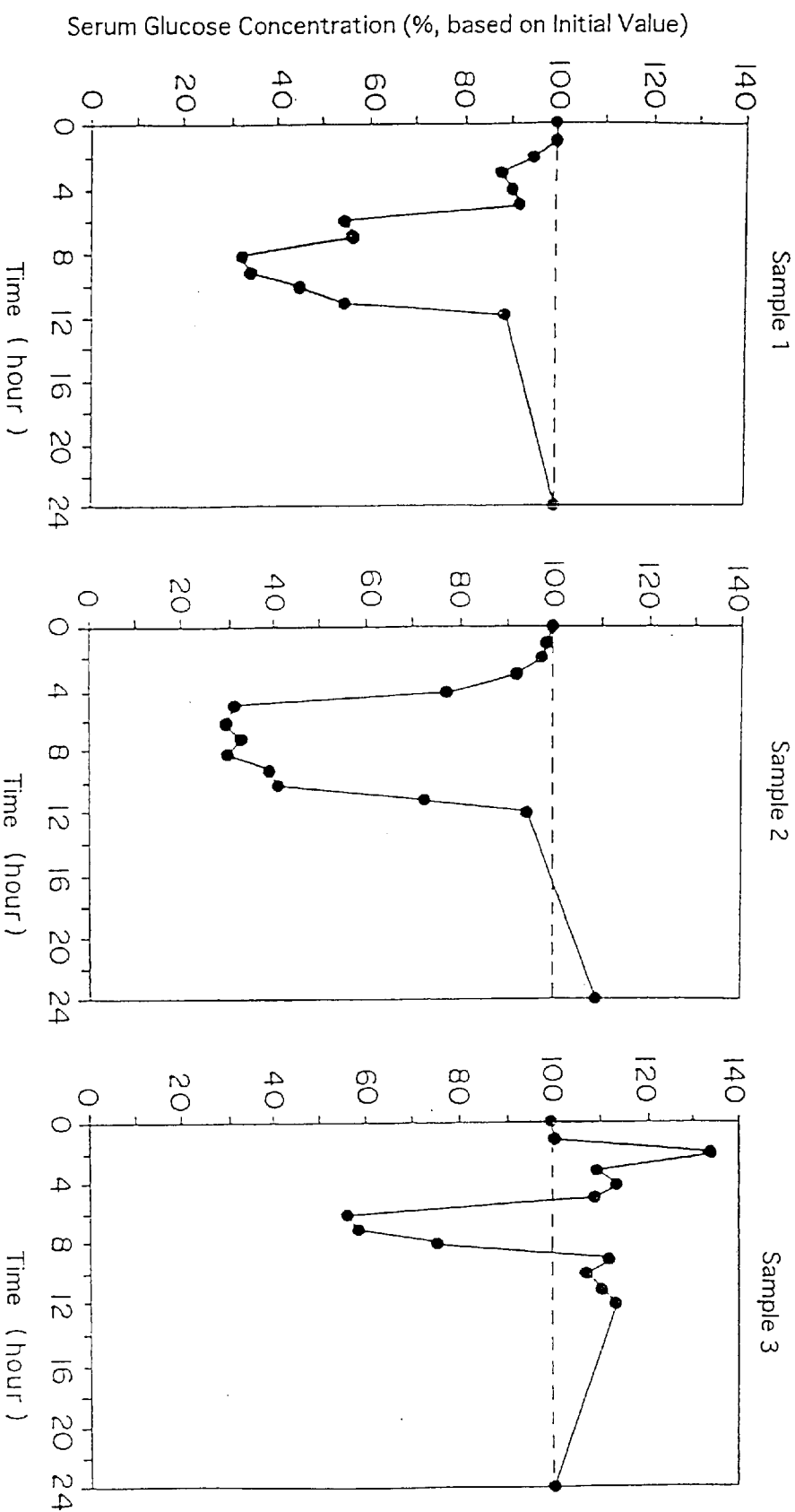
FIG. 7 is a graph showing the change in glucose level in plasma as a function of time in beagle dogs in fasted condition having received a colon-specific drug release system of the present invention containing insulin (Example 10).
Figure 8:
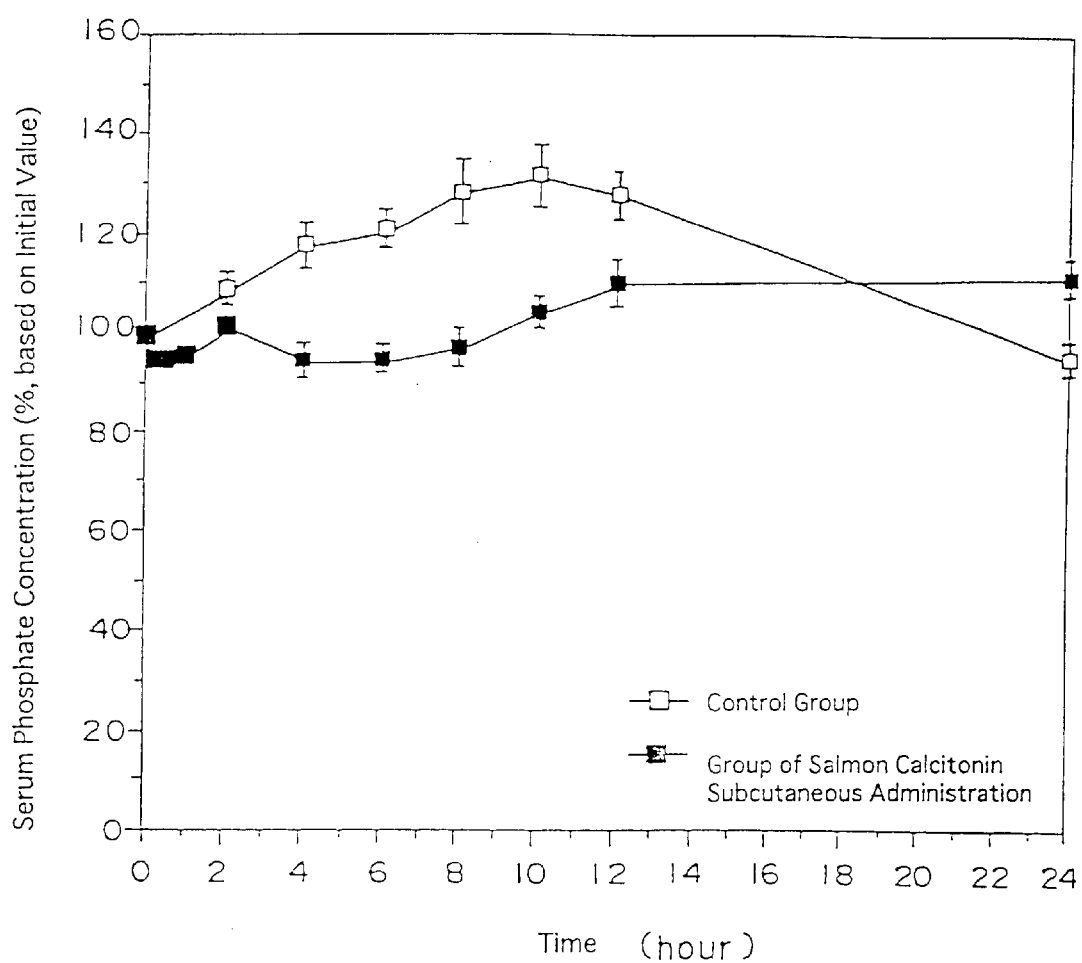
FIG. 8 is a graph showing the change in phosphorusl concentration in plasma as a function of time in beagle dogs in fasted condition having subcutaneously received salmon calcitonin along with the results of a control group (untreated) (Test Example 6).

As shown in FIG. 7, insulin absorption was improved by incorporating Eudragit RS100L into Eudragit E100.

EXAMPLES 11 TO 12

| | Example 11 | Example 12 |
|---|---|---|
| Insulin | 10 mg | 10 mg |
| Lactulose | 100 mg | 130 mg |
| Meglumine | 30 mg | 30 mg |
| Citric acid | 10 mg | 10 mg |
| Glycocholate Na | 100 mg | 100 mg |
| EDTA2Na | 50 mg | — |
| Sodium caprate | — | 10 mg |
| Total: | 300 mg | 290 mg |

Insulin, lactulose, and other additives were mixed in a mortar and made to prepare tablets. In the same manner as in Example 4, the tablets were successively coated with 11 wt % of Eudragit E100/Eudragit RS100L (9/1), 1 wt % of TC5E, and 11 wt % of Eudragit L100/castor oil (5/1) in this order by means of a Hicoater to obtain a preparation of the present invention.

Two tablets of the preparation were orally administered to beagle dogs in fasted condition together with 30 ml of water, and blood was taken with time to determine the glucose level in plasma.

As a result, insulin absorption was improved.

EXAMPLES 13 TO 17

| | 13 | 14 | 15 | 16 | 17 |
|---|---|---|---|---|---|
| Insulin | 20 | 20 | 20 | 20 | 20 |
| Lactulose | 108 | 120 | 130 | 70 | 100 |
| Meglumine | 30 | 30 | 30 | 30 | 30 |
| Citric acid | 10 | 10 | 10 | 10 | 10 |
| Sugar Ester L1695 | — | 36 | — | — | 30 |
| Sodium laurylsulfate | 12 | 12 | 60 | 60 | 60 |
| Camostat mesilate | — | — | — | 10 | 10 |
| 1-Menthol | — | — | 30 | — | — |
| Total: | 180 mg | 228 mg | 280 mg | 200 mg | 260 mg |

Insulin, lactulose, and other additives were mixed in a mortar and made to prepare tablets. In the same manner as in Example 4, the tablets were successively coated with 11 wt % of Eudragit E100/Eudragit RS100L (9/1), 1 wt % of TC5E, and 11 wt % of Eudragit L100/castor oil (5/1) in this order by means of a Hicoater to obtain a preparation of the present invention.

One tablet of the preparation was orally administered to beagle dogs in fasted condition together with 30 ml of water, and blood was taken with time to determine the glucose level in plasma.

As a result, an improvement in insulin absorption was observed.

EXAMPLES 18 AND 19

| | Example 18 | Example 19 |
|---|---|---|
| Insulin | 10 mg | 10 mg |
| Lactulose | 125 mg | 100 mg |
| Meglumine | 30 mg | 30 mg |
| Citric acid | 10 mg | 10 mg |
| Glycocholate Na | 100 mg | 100 mg |
| Polyethylene oxide coagulant | 8.25 mg | 12.5 mg |
| Total: | 283.25 mg | 262.5 mg |

Insulin, lactulose, and other additives were mixed in a mortar and made to prepare tablets. In the same manner as in Example 4, the tablets were successively coated with 11 wt % of Eudragit E100/Eudragit RS100L (9/1), 1 wt % of TC5E, and 11 wt % of Eudragit L100/castor oil (5/1) in this order by means of a Hicoater to obtain a preparation of the present invention.

Two tablets of the preparation of Example 18 were orally administered to beagle dogs in fasted condition together with 30 ml of water, and blood was taken with time to determine the glucose level in plasma.

The insulin absorption time was prolonged for 3 to 5 hours by addition of 3% polyethylene oxide (8.25 mg).

EXAMPLE 20

| | |
|---|---|
| Insulin | 10 mg |
| Lactulose | 100 mg |
| Meglumine | 30 mg |

| -continued | |
|---|---|
| Citric acid | 13 mg |
| Sodium glycocholate | 100 mg |
| Total: | 253 mg |

Insulin, lactulose, and other additives were mixed in a mortar and made to prepare tablets. In the same manner as in Example 4, the tablets were successively coated with 11 wt % of Eudragit E100/Eudragit RS100L (9/1), 1 wt % of TC5E, and 11 wt % of Eudragit L100/castor oil (5/1) in this order by means of a Hicoater to obtain a preparation of the present invention.

Two tablets of the preparation were orally administered to beagle dogs in fasted condition together with 30 ml of water, and blood was taken with time to determine the glucose level in plasma.

As a result, the absorption initiation time was shortened, and an improvement in absorption was observed. This seems to be because the increase in amount of citric acid slightly reduced pH but to a degree that Eudragit E100 still remains undissolved, so that the pH is swiftly shifted to a value at which Eudragit E100 can dissolve as soon as fermentation by the action of enterobacterial starts.

EXAMPLES 21 TO 24

| | 21 | 22 | 23 | 24 |
|---|---|---|---|---|
| Salmon calcitonin | 500 IU | 500 IU | 250 IU | 500 IU |
| Lactulose | 100 mg | 100 mg | 100 mg | 100 mg |
| Meglumine | 30 mg | 30 mg | 30 mg | 30 mg |
| Citric acid | 13 mg | 13 mg | 13 mg | 13 mg |
| Glycocholate Na | 100 mg | 100 mg | 100 mg | 100 mg |
| EDTA2Na | — | 50 mg | 50 mg | — |
| Sodium caprate | — | — | — | 50 mg |

Salmon calcitonin, lactulose, and other additives were mixed in a mortar and made to prepare tablets. In the same manner as in Example 4, the tablets were successively coated with 11 wt % of Eudragit E100/Eudragit IS100L (9/1), 1 wt % of TC5E, and 11 wt % of Eudragit L100/castor oil (5/1) in this order by means of a Hicoater to obtain a preparation of the present invention.

A single tablet of the preparation obtained in Examples 21, 22 or 24 or two tablets of the preparation obtained in Example 23 was administered orally to beagle dogs together with 30 ml of water, and blood was taken with time to determine the phosphorus concentration in plasma.

In all the formulations, a reduction in phosphorus concentration in plasma was observed when compared with the respective control group.

EXAMPLES 25 TO 28

| | 25 | 26 | 27 | 28 |
|---|---|---|---|---|
| Salmon calcitonin | 500 IU | 500 IU | 250 IU | 500 IU |
| Lactulose | 100 mg | 100 mg | 100 mg | 100 mg |
| Meglumine | 30 mg | 30 mg | 30 mg | 30 mg |
| Citric acid | 13 mg | 13 mg | 13 mg | 13 mg |
| Sugar ester L1695 | 100 mg | 100 mg | 100 mg | 100 mg |
| EDTA2Na | — | 50 mg | 50 mg | — |
| Sodium caprate | — | — | — | 50 mg |

Salmon calcitonin, lactulose, and other additives were mixed in a mortar and made to prepare tablets. In the same manner as in Example 4, the tablets were successively coated with 11 wt % of Eudragit E100/Eudragit RS100L (9/1), 1 wt % of TC5E, and 11 wt % of Eudragit L100/castor oil (5/1) in this order by means of a Hicoater to obtain a preparation of the present invention.

A single tablet of the preparation obtained in Examples 25, 26 or 28 or two tablets of the preparation obtained in Example 27 was administered orally to beagle dogs together with 30 ml of water, and blood was taken with time to determine the phosphorus concentration in plasma.

In all the formulations, a reduction in phosphorus concentration in plasma was observed when compared with the respective control group. The results obtained in Example 28 are shown in FIG. 9.

Figure 9:
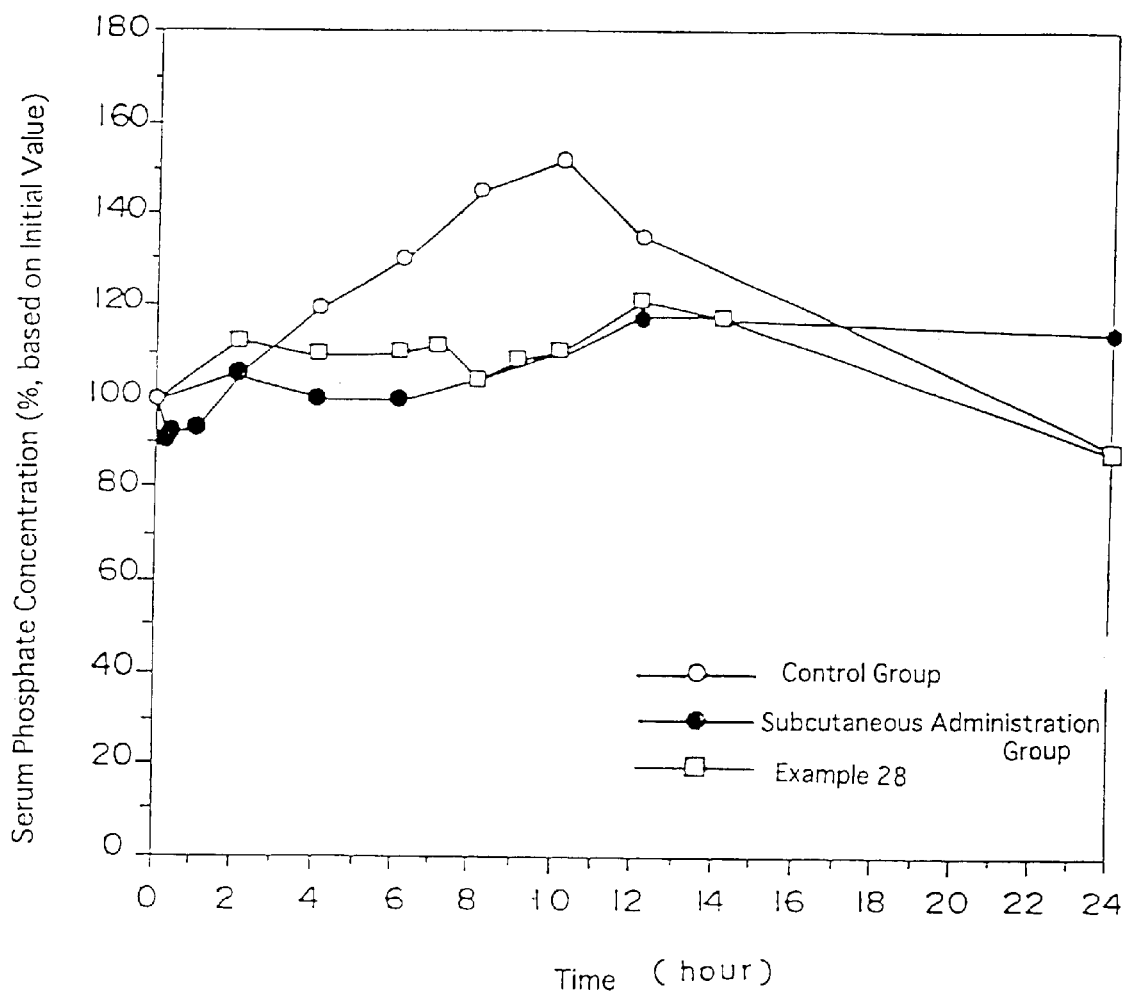
FIG. 9 is a graph showing the charge in phosphorus concentration in plasma as a function of time in beagle dogs in fasted condition having received a colon-specific drug release system containing salmon calcitonin (Example 28) along with the results of a control group (untreated) and a group of subcutaneous administration.
Figure 10:
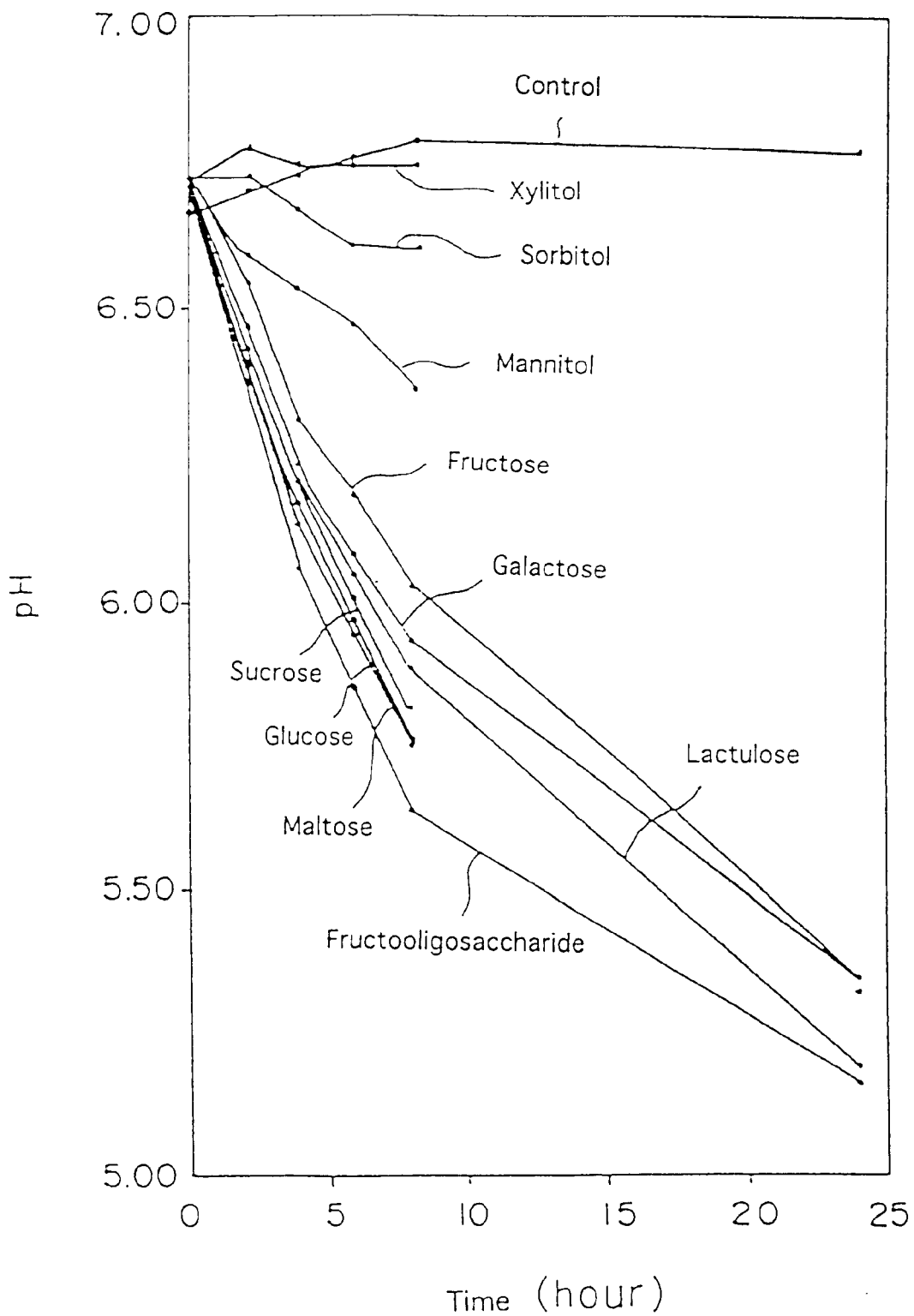
FIG. 10 is a graph showing the change in pH as a function of time in an isotonic phosphate buffer solution containing the cecal contents of a rat in fasted condition to which a saccharide of various kinds has been added (Test Example 7).

FIG. 9 shows the changes in average phosphorus concentration in plasma in the group administered the preparation of Example 28 (500 IU/animal, n=3), in the control group (untreated, n=3), and in the group subcutaneously administered the preparation (50 IU/animal, n=3).

In the control group, the phosphorus concentration in plasma increased as a function of time from the very beginning of blood collection, reached the maximum of 150% after 10 hours from the start of the test, and then descended. To the contrary, the phosphorus concentration in plasma in the group of subcutaneous administration was suppressed immediately after the administration (the effect of the drug does not reach saturation at this dose of 50 IU/animal). In the group of the preparation of Example 28, although the phosphorus concentration measured at a 2-hour point shows an increase similarly to the control group, a significant action of suppressing the rise in phosphorus level was observed on and after a 4-hour point since the drug is not released until the preparation reaches the colon, and absorption of salmon calcitonin was confirmed. The effect was considered to be equal to that obtained in subcutaneous administration.

The similar effects were observed in Examples 21 to 27.

EXAMPLE 29

| | |
|---|---|
| Insulin | 10 mg |
| Meglumine | 30 mg |
| Citric acid | 10 mg |
| Glycocholate Na | 100 mg |
| Total: | 150 mg |
| Lactulose | 100 mg |

Insulin, meglumine, citric acid, and glycocholate Na were mixed in a mortar to prepare tablets. The tablets were coated with 11 wt % of Eudragit E100 by means of a Hicoater. The coated tablets were further coated with 11 wt % of Eudragit L100/castor oil (5/1) by means of a Hicoater. Separately, lactulose was made into tablets and coated with 11 wt % of Eudragit L100/castor oil (5/1) by means of a Hicoater. Each one of the two kinds of tablets were put in a gelatin capsules to prepare a preparation of the present invention.

EXAMPLE 30

| Insulin | 10 mg |
|---|---|
| Meglumine | 30 mg |
| Citric acid | 10 mg |
| Glycocholate Na | 100 mg |
| Total: | 150 mg |

Insulin, meglumine, citric acid, and sodium glycocholate Na were mixed in a mortar to prepare tablets. The tablets were coated with 2 wt % of Eudragit E100 (Hicoater). The coated tablets were further coated successively with 2 wt % of Eudragit E100/lactulose (5/1), 2 wt % of Eudragit E100/lactulose (2/1), 2 wt % of Eudragit E100/lactulose (1/1) (Hicoater), 2 wt % of Eudragit E100/lactulose (1/2), and finally, 11 wt % of Eudragit L100/castor oil (5/1) (Hicoater) to prepare a preparation of the present invention.

EXAMPLE 31

| Insulin | 10 mg |
|---|---|
| Meglumine | 30 mg |
| Citric acid | 10 mg |
| Glycocholate Na | 100 mg |
| Total: | 150 mg |
| Lactulose | 50 mg |
| TC-5 | adequate amount |

Insulin, meglumine, citric acid, and glycocholate Na were mixed in a mortar to prepare tablets. The tablets were coated with 11 wt % of Eudragit E100 (Hicoater). The coated tablets were coated with lactulose using a TC-5 solution as a binder to have a lactulose coating weight of 50 mg per tablet. The tablets were further coated with Eudragit L100/castor oil (5/1) (Hicoater) to obtain a preparation of the present invention.

EXAMPLE 32

| Insulin | 10 mg |
|---|---|
| Meglumine | 30 mg |
| Citric acid | 10 mg |
| Glycocholate Na | 100 mg |
| Lactulose | 100 mg |
| Total: | 250 mg |

Insulin, meglumine, citric acid, and sodium glycocholate were mixed in a mortar to prepare tablets. The tablets were coated with lactulose and then further coated successively with 11 wt % of Eudragit E100, 2 wt % of TC5E, and 11 wt % of Eudragit L100/castor oil (5/1) (Hicoater) to obtain a preparation of the present invention.

EXAMPLE 33

| Tablet 1 | |
|---|---|
| Insulin | 10 mg |
| Meglumine | 30 mg |
| Citric acid | 10 mg |
| Glycocholate Na | 100 mg |
| Total: | 150 mg |

| Tablet 2 | |
|---|---|
| Lactulose | 100 mg |

Insulin, meglumine, citric acid, and glycocholate Na were mixed in a mortar to prepare tablets. The tablets were coated with 11 wt % of Eudragit E100 (Hicoater). Lactulose was made into tablets and coated with 11 wt % of Eudragit L100 (Hicoater). The two tablets were put in a gelatin capsule, and the capsules were further coated with 11 wt % of Eudragit L100/castor oil (5/1) (Hicoater) to obtain a preparation of the present invention.

EXAMPLE 34

| Insulin | 10 mg |
|---|---|
| Meglumine | 30 mg |
| Citric acid | 10 mg |
| Glycocholate Na | 100 mg |
| Total: | 150 mg |

Insulin, meglumine, citric acid, and glycocholate Na were mixed in a mortar to prepare tablets. The tablets were coated with 4 wt % of AEA/lactulose (8/1) (Hicoater). The tablets were further coated successively with 2 wt % AEA/lactulose (4/1), 2 wt % of AEA/lactulose (2/1), 2 wt % of AEA/lactulose (1/1) (Hicoater), and 2 wt % of AEA/lactulose (1/2). Finally, the tablets were coated with 11 wt % of Eudragit L100/castor oil (5/1) (Hicoater) to obtain a preparation of the present invention.

EXAMPLE 35

| Insulin | 10 mg |
|---|---|
| Meglumine | 30 mg |
| Citric acid | 10 mg |
| Glycocholate Na | 100 mg |
| Total: | 150 mg |
| Lactulose | 100 mg |

Insulin, meglumine, citric acid, and glycocholate Na were mixed in a mortar to prepare tablets. The tablets were coated with 11 wt % of Eudragit E100 (Hicoater). The coated tablets were then coated successively with 100 mg of lactulose using TC5E as a binder, 11 wt % of Eudragit E100, and 11 wt % of Eudragit L100/castor oil (5/1) (Hicoater) to obtain a preparation of the present invention.

What is claimed is:

1. An oral drug delivery system for releasing a drug specifically in the colon of the gastrointestinal tract, wherein said system comprises a drug (b) coated with a pharmaceutically acceptable acrylic or cellulosic organic acid-soluble polymer material which dissolves at a pH lower than 6 (a), in an amount of from 2.5% to 40% and a saccharide (c) comprising lactulose which rapidly generates an organic acid by the action of enterobacteria in the lower part of the gastrointestinal tract in an amount of from 10% to 99.9%, wherein said composition comprising the drug (b) coated with the organic acid-soluble polymer material (a) and saccharide (c) is further coated with a pharmaceutically acceptable enteric coating polymer material which dissolves at a pH not lower than 6 (d) and wherein said composition when orally administered, is delivered to the lower part of the gastrointestinal tract without releasing the drug (b) at the upper part of the gastrointestinal tract and, at the lower part of the gastrointestinal tract, the polymer (a) coating the drug (b) is dissolved by organic acids generated by degradation of the saccharide (c) by the enterobacteria, and wherein the system is in the form of a tablet or granule.

2. An oral drug delivery system for releasing a drug specifically in the colon of the gastrointestinal tract, which comprises a drug (b) coated with a pharmaceutically acceptable acrylic or cellulosic organic acid-soluble polymer material which dissolves at a pH lower than 6 (a) in an amount of from 2.5% to 40% and a saccharide (c) comprising lactulose in an amount of from 10% to 99.9% which rapidly generates an organic acid by the action of enterobacteria in the lower part of the gastrointestinal tract, said system being further coated with a pharmaceutically acceptable enteric coating polymer material which dissolves at a pH not lower than 6 (d) and wherein said system, when orally administered, is delivered to the lower part of the gastrointestinal tract without releasing the drug (b) at the upper part of the gastrointestinal tract and, at the lower part of the gastrointestinal tract, the polymer (a) coating the drug (b) is dissolved by organic acids generated by degradation of the saccharide (c) by the enterobacteria and wherein the system is in the form of a tablet or granule.

3. A colon-specific drug release oral composition, which comprises a drug (b) coated with a pharmaceutically acceptable acrylic or cellulosic organic acid-soluble polymer material which dissolves at a pH lower than 6 (a) in an amount of from 2.5% to 40% and a saccharide (c) comprising lactulose in an amount of from 10% to 99.9% which rapidly generates an organic acid by the action of enterobacteria in the lower part of the gastrointestinal tract, said composition being coated with a pharmaceutically acceptable enteric coating polymer material which dissolves at a pH not lower than 6 (d) and wherein said system, when orally administered, is delivered to the lower part of the gastrointestinal tract without releasing the drug (b) at the upper part of the gastrointestinal tract and, at the lower part of the gastrointestinal tract, the polymer (a) coating the drug (b) is dissolved by organic acids generated by degradation of the saccharide (c) by the enterobacteria and wherein said composition is in the form of a tablet or granule.

4. A method for releasing a drug specifically in the colon of the gastrointestinal tract of a host which comprises administering to the host a composition comprising a drug (b) coated with a pharmaceutically acceptable acrylic or cellulosic organic acid-soluble polymer material which dissolves at a pH lower than 6 (a) in an amount of from 2.5% to 40% and a saccharide (c) comprising lactulose in an amount of from 10% to 99.9% which rapidly generates an organic acid by the action of enterobacteria in the lower part of the gastrointestinal tract, said composition further being coated with a pharmaceutically acceptable enteric coating polymer material which dissolves at a pH not lower than 6 (d) and wherein said composition when orally administered, is delivered to the lower part of the gastrointestinal tract without releasing the drug (b) at the upper part of the gastrointestinal tract and, at the lower part of the gastrointestinal tract, the polymer (a) coating the drug (b) is dissolved by organic acids generated by degradation of the saccharide (c) by the enterobacteria, and wherein said composition is in the form of a tablet or granule.

5. The method of claim 4, wherein the saccharide (c) is present as a mixture with the drug (b).

6. The method of claim 4, wherein the saccharide (c) is provided as a coating layer on the drug (b) coated with the organic acid-soluble polymer material (a).

7. The system of claim 1, wherein the saccharide (c) is present as a mixture with the drug (b).

8. The system of claim 1, wherein the organic acid-soluble polymer material (a) is at least one polymer which dissolves at pH lower than 5.5.

9. The system of claim 8 wherein the organic acid-soluble polymer material (a) is at least one member selected from the group consisting of dimethylaminoethyl methacrylate-methyl methacrylate copolymer, polyvinyl acetal diethylaminoacetate and chitosan.

10. The system of claim 1, wherein the enteric coating (d) is at least one member selected from the group consisting of a methyl methacrylate-methacrylate acid (1:1) copolymer, a methyl methacrylate-methacrylate acid (2:1) copolymer, an ethyl acrylate-methacrylic acid (1:1) copolymer, hydroxypropylmethylcellulose phthalate, cellulose acetate phthalate, and shellac.

11. The system of claim 1, wherein the drug (b) comprises a peptide, a protein, or a derivative thereof.

12. The colon-specific drug release oral composition of claim 3, wherein the saccharide (c) is present as a mixture with the drug (b).

13. The colon-specific drug release oral composition of claim 3, wherein the organic acid-soluble polymer material (a) is at least one polymer which dissolves at pH lower than 5.5.

14. The colon specific drug release oral composition of claim 3, wherein the organic acid-soluble polymer material (a) is at least one member selected from the group consisting of a dimethylaminoethyl methacrylate-methyl methacrlate copolymer, polyvinyl acetal diethylaminoacetate and chitosan.

15. The method of claim 3, wherein the enteric coating (d) is at least one member selected from the group consisting of a methyl methacrylate-methylacrylate acid (1:1) copolymer, a methyl methacrylate-methacrylate acid (2:1) copolymer, an ethyl acrylate-methacrylic acid (1:1) copolymer, hydroxypropylmethylcellulose phthalate, cellulose acetate phthalate, and shellac.

16. The colon-specific drug release oral composition of claim 3, wherein the drug (b) comprises a peptide, a protein, or a derivative thereof.

* * * * *

UNITED STATES PATENT AND TRADEMARK OFFICE
CERTIFICATE OF CORRECTION

PATENT NO. : 6,368,629 B1  Page 1 of 1
DATED : April 9, 2002
INVENTOR(S) : Watanabe et al.

It is certified that error appears in the above-identified patent and that said Letters Patent is hereby corrected as shown below:

Column 28,
Line 33, please delete "a methyl methacrylate-methacrylate acid (1:1) copolymer" and insert -- a methyl methacrylate-methylacrylate acid (1:1) co polymer --.
Line 50, please delete "methacrlate" and insert -- methacrylate --.

Signed and Sealed this

Eighteenth Day of February, 2003

JAMES E. ROGAN
*Director of the United States Patent and Trademark Office*